United States Patent
Stauffer et al.

(10) Patent No.: US 9,456,997 B2
(45) Date of Patent: Oct. 4, 2016

(54) SELECTIVE INHIBITION OF β1-ADRENERGIC RECEPTORS FOR THE TREATMENT OF PEDIATRIC HEART FAILURE

(75) Inventors: Brian Stauffer, Aurora, CO (US); Carmen Sucharov, Aurora, CO (US); Shelley Miyamoto, Aurora, CO (US)

(73) Assignee: THE REGENTS OF THE UNIVERSITY OF COLORADO, A BODY CORPORATE, Denver, CO (US)

(*) Notice: Subject to any disclaimer, the term of this patent is extended or adjusted under 35 U.S.C. 154(b) by 215 days.

(21) Appl. No.: 13/817,969

(22) PCT Filed: Aug. 25, 2011

(86) PCT No.: PCT/US2011/049123
§ 371 (c)(1),
(2), (4) Date: Jun. 6, 2013

(87) PCT Pub. No.: WO2012/027557
PCT Pub. Date: Mar. 1, 2012

(65) Prior Publication Data
US 2013/0296416 A1    Nov. 7, 2013

Related U.S. Application Data

(60) Provisional application No. 61/377,277, filed on Aug. 26, 2010.

(51) Int. Cl.
*A61K 31/137* (2006.01)
*A61K 31/138* (2006.01)
*A61K 31/352* (2006.01)
*A61K 45/06* (2006.01)
(Continued)

(52) U.S. Cl.
CPC .......... *A61K 31/137* (2013.01); *A61K 31/138* (2013.01); *A61K 31/165* (2013.01); *A61K 31/35* (2013.01); *A61K 31/352* (2013.01); *A61K 45/06* (2013.01)

(58) Field of Classification Search
CPC ............. A61K 31/137; A61K 31/138; A61K 31/165; A61K 31/35; A61K 31/352; A61K 45/06
See application file for complete search history.

(56) References Cited

U.S. PATENT DOCUMENTS

| 6,545,040 B1 | 4/2003 | Xhonneux et al. |
| 2007/0014733 A1 | 1/2007 | O'Donnell et al. |

(Continued)

FOREIGN PATENT DOCUMENTS

| WO | WO2006130174 | * 12/2006 | ........... A61K 31/352 |
| WO | WO 2009/138451 | 11/2009 | |

OTHER PUBLICATIONS

Ahmet et al., "Beneficial effects of chronic pharmacological manipulation of beta-adrenoreceptor subtype signaling in rodent dilated ischemic cardiomyopathy", *Circulation*, 110:1083-1090, 2004.

(Continued)

*Primary Examiner* — Savitha Rao
(74) *Attorney, Agent, or Firm* — Parker Highlander PLLC

(57) ABSTRACT

Provided are methods of treating heart failure in children using B1-selective adrenergic receptor antagonists, alone or in combination with other agents, including B-2-selective adrenergic receptor agonists.

12 Claims, 12 Drawing Sheets

(51) Int. Cl.
*A61K 31/165* (2006.01)
*A61K 31/35* (2006.01)

(56) References Cited

U.S. PATENT DOCUMENTS

| | | | |
|---|---|---|---|
| 2007/0014734 | A1 | 1/2007 | O'Donnell et al. |
| 2007/0259950 | A1 | 11/2007 | Sheth et al. |
| 2009/0215844 | A1 | 8/2009 | Davis et al. |
| 2009/0227646 | A1 | 9/2009 | Davis et al. |

OTHER PUBLICATIONS

Ahmet et al., "Cardioprotective and survival benefits of long-term combined therapy with beta2 adrenoreceptor (AR) agonist and beta1 AR blocker in dilated cardiomyopathy postmyocardial infarction", *JPET*, 325:491-499, 2008.

Ahmet et al., "Pharmacological stimulation of beta2-adrenergic receptors (beta2AR) enhances therapeutic effectiveness of beta1AR blockade in rodent dilated ischemic cardiomyopathy", *Heart Failure Rev.*, 10:289-296, 2005.

Baker, "The selectivity of β-adrenoreceptor antagonists at the human β1, β2 and β3 adrenoreceptors", *British Journal of Pharmacology*, 144:317-322, 2005.

Bartholomeu et al., "Intracellular mechanisms of specific beta-adrenoceptor antagonists involved in improved cardiac function and survival in a genetic model of heart failure", *J. Mol. Cell Cardiol.*, 45:240-249, 2008.

Boknik et al., "Protein phosphatase activity is increased in a rat model of long-term beta-adrenergic stimulation", *Naunyn. Schmiedebergs Arch. Pharmacol.*, 362:222-231, 2000.

Bristow and Feldman, "Changes in the receptor-G protein-adenylyl cyclase system in heart failure from various types of heart muscle disease", *Basic Res. Cardiol.*, 87(Suppl 1):15-35, 1992.

Bristow et al., "Beta 1- and beta 2-adrenergic receptor subpopulations in nonfailing and failing human ventricular myocardium: coupling of both receptor types to muscle contraction and selective beta 1-receptor down-regulation in the heart", *Circulation Research*, 59: 297-309, 1986.

Brixius et al., "Nebivolol, bucindolol, metoprolol and carvedilol are devoid of intrinsic sympathomimetic activity in human myocardium", *British Journal of Pharmacology*, 133:1330-1338, 2001.

Cheng, "Nebivolol: A Third-Generation β-Blocker for Hypertension", *Clinical Therapeutics*, 31(3): 447-462, 2009.

Dalla Libera et al., "Skeletal muscle proteins oxidation in chronic right heart failure in rats: can different beta-blockers prevent it to the same degree?", *Int. J. Cardiol.*, 143:192-199, 2010.

Foerster et al., "Pediatric heart failure therapy with beta-adrenoceptor antagonists", *Pediatric Drugs*, 10(2):125-134, 2008.

Harding et al., "Cardiac beta ARK 1 inhibition prolongs survival and augments beta blocker therapy in a mouse model of severe heart failure", *Proc. Natl. Acad. Sci. USA*, 98:5809-5814, 2001.

International Preliminary Report on Patentability issued in International Application No. PCT/US11/49123, mailed Mar. 7, 2013.

International Preliminary Report and Written Opinion issued in International Application No. PCT/US11/49123, mailed Jan. 27, 2012.

International Preliminary Report and Written Opinion issued in International Application No. PCT/US11/48942, mailed Apr. 10, 2012.

Kilinc et al., "Adrenomedullin and nitrite levels in children with dilated cardiomyopathy", *Pediatric Cardiology*, 24(4):381-385, 2003.

Kozlik et al., "Myocardial beta-adrenoreceptor density and the distribution of beta-1 and beta-2 adrenoreceptor subpopulations in children with congenital heart disease," *Eur J Pediatrics*, 150(6): 388-94, 1991.

Kozlik-Feldmann et al., "Distribution of myocardial beta-adrenoreceptor subtypes and coupling to the adenylate cyclase in children with congenital heart disease and implications for treatment", *Clin Pharmacology*, 33(7): 588-95, 1993.

Lowes et al., "Myocardial gene expression in dilated cardiomyopathy treated with beta-blocking agents", *N. Engl. J. Med.*, 346:1357-1365, 2002.

Milting et al., "Selective upregulation of beta1-adrenergic receptors and dephosphorylation of troponin I in end-stage heart failure patients supported by ventricular assist devices", *J. Mol. Cell Cardiol.*, 41:441-450, 2006.

Moen and Wagstaff, "Nebivolol: A Review of its Use in the Management of Hypertension and Chronic Heart Failure", *Adis Drug Evaluation*, 6(10); 1359-1409, 2006.

Moffett et al., "Future pharmacologic agents for treatment of heart failure in children", *Pediatr Cardiol.*, 27:533-551, 2006.

Shaddy et al., "Carvedilol for Children and Adolescents with Heart Failure: *A* Randomized Controlled Trial", *JAMA*, 298(10): 1171-1179, 2007.

Whaley-Connell et al., "Nebivolol reduces proteinuria and renal NADPH oxidase-generated reactive oxygen species in the transgenic Ren2 rat", *Am. J. Nephrol.*, 30:354-360, 2009.

* cited by examiner

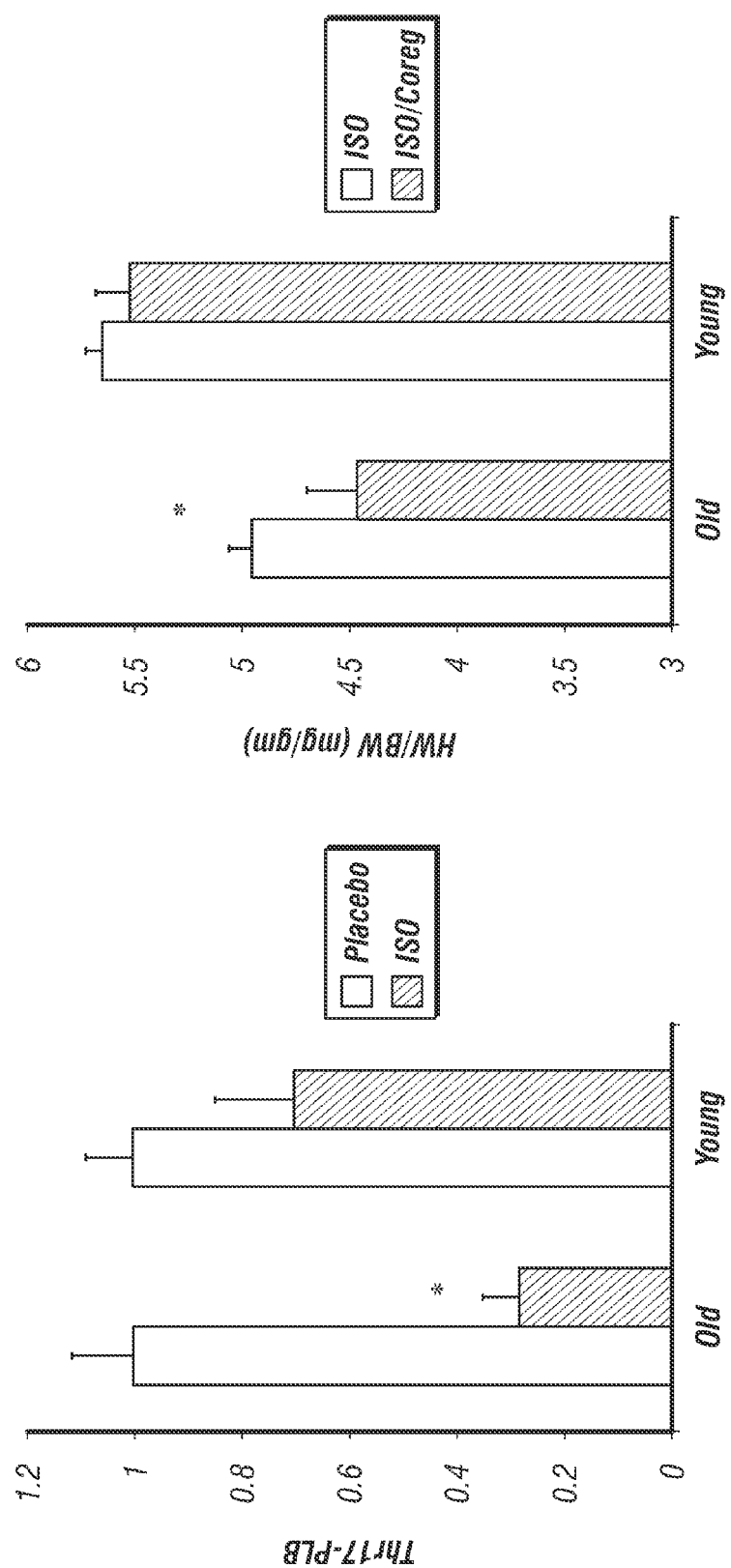

SEQUENCE LISTING

```
<160> NUMBER OF SEQ ID NOS: 16

<210> SEQ ID NO 1
<211> LENGTH: 28
<212> TYPE: DNA
<213> ORGANISM: Artificial Sequence
<220> FEATURE:
<223> OTHER INFORMATION: Synthetic primer

<400> SEQUENCE: 1
agttcaatca cttggcgtga cttcacta                                      28

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
cctgggcact cttttgctta                                               20

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
ggtgctgccc cagatgatt                                                19

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
ctggagactg gctaggactt c                                             21

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
cctgtccagc agaaagagc                                                19

<210> SEQ ID NO 6
<211> LENGTH: 31
<212> TYPE: DNA
<213> ORGANISM: Artificial Sequence
<220> FEATURE:
<223> OTHER INFORMATION: Synthetic primer

<400> SEQUENCE: 6
caggcaaagt caagcattca tatttattgt g                                  31
```

-continued

```
<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
cgctcagtca tggcggat                                                   18

<210> SEQ ID NO 8
<211> LENGTH: 17
<212> TYPE: DNA
<213> ORGANISM: Artificial Sequence
<220> FEATURE:
<223> OTHER INFORMATION: Synthetic primer

<400> SEQUENCE: 8
gccccaaatg cagccat                                                    17

<210> SEQ ID NO 9
<211> LENGTH: 17
<212> TYPE: DNA
<213> ORGANISM: Artificial Sequence
<220> FEATURE:
<223> OTHER INFORMATION: Synthetic primer

<400> SEQUENCE: 9
ggccagatcg cgctaca                                                    17

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
gggccaatta gagagcaggt tt                                              22

<210> SEQ ID NO 11
<211> LENGTH: 18
<212> TYPE: DNA
<213> ORGANISM: Artificial Sequence
<220> FEATURE:
<223> OTHER INFORMATION: Synthetic primer

<400> SEQUENCE: 11
gcgaaggtca agctgctt                                                   18

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
ctgggctcca atcctgtcaa t                                               21

<210> SEQ ID NO 13
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 13
gggcatcatc atgggcgtct t                                           21

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
ttcaccacgt tggccaggaa g                                           21

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
caagtaccag agcctgctga ccaa                                        24

<210> SEQ ID NO 16
<211> LENGTH: 24
<212> TYPE: DNA
<213> ORGANISM: Artificial Sequence
<220> FEATURE:
<223> OTHER INFORMATION: Synthetic primer

<400> SEQUENCE: 16
ggaggtaagg cctgacacaa tcca                                        24
```

SELECTIVE INHIBITION OF β1-ADRENERGIC RECEPTORS FOR THE TREATMENT OF PEDIATRIC HEART FAILURE

The present application is a national phase application under 35 U.S.C. §371 of International Application No. PCT/US2011/049123, filed Aug. 25, 2011, which claims benefit of priority to U.S. Provisional Application Ser. No. 61/377,277, filed Aug. 26, 2010, the entire content of each of the above-referenced disclosures is specifically incorporated herein by reference.

This invention was made with government support under grant no. NIH R21 HL097123 awarded by the National Institutes of Health. The government has certain rights in the invention.

BACKGROUND OF THE INVENTION

1. Field of the Invention

The present invention relates generally to the fields of pathology and pediatric medicine. More particularly, it concerns treatment of pediatric heart failure using β1-selective adrenergic receptor antagonists.

2. Description of Related Art

In contrast to adult heart failure, the pathophysiology of the development of myocardial dysfunction and heart failure in children is poorly understood. In patients with heart failure, as with many other disease processes, it does not appear that children are simply small adults. The details supporting this statement are extensively outlined below. For example, children with heart failure do not demonstrate the beneficial effects that are observed in adults treated with nonselective β-adrenergic receptor antagonist drugs, or β-blocking agents. β blockers have clear benefit for the treatment of heart failure in adults as they block the adverse effects secondary to the elevated blood catecholamines present in patients suffering from heart failure. Importantly, β blockers have different subtype specificity. For example, carvedilol blocks β2 receptors up to 7 times greater than β1 receptors and also blocks α-adrenergic receptors. In contrast, metoprolol selectively blocks the β1 receptor. Both agents have been approved by the FDA for treatment of heart failure in adults.

In contrast to the reproducible clinical benefits of β blockers in adults, a recent clinical trial (The Pediatric Carvedilol Trial) demonstrated no clinical benefit for Carvedilol, a nonselective β adrenergic receptor antagonist, in children with heart failure (Shaddy, JAMA). Additionally, while both children and adults have increased mortality in response to β-agonist therapy, such as dobutamine, phosphodiesterase inhibitors such as milrinone are not associated with increased mortality in children. On the other hand, phosphodiesterase therapy in adults is associated with early cardiovascular mortality and increased risk of arrhythmia development. From a therapeutic standpoint these characteristics indicate that children with heart failure represent a population with unique needs and provide an opportunity for the development of novel therapeutics or new indications for existing therapeutic modalities.

SUMMARY OF THE INVENTION

Thus, in accordance with the present invention, there is provided a method of treating heart failure in a pediatric subject comprising administering to said subject an effective amount of a β1-adrenergic receptor-selective antagonist. The pediatric subject may be less than 15 years of age, less than 12 years of age, less than 10 years of age, or less than 8 years of age. The β1-adrenergic receptor-selective antagonist may be at least twice as β1-selective as Metoprolol, three times as β1-selective as Metoprolol, five times as β1-selective as Metoprolol, or 10 times as β1-selective as Metoprolol. The pediatric subject may suffer from systemic ventricular failure. Ventricular failure could result from dilated cardiomyopathy due to idiopathic, post-viral, including coxsackie virus, parvovirus, enterovirus, influenza, or echovirus, familial or genetic causes, such as Fabrys disease, familial dilated cardiomyopathy, Barth syndrome, Kearns-Sayre syndrome, Troponin T or beta-myosin heavy chain mutation; or could be secondary to neuromuscular diseases, such as Duschennes muscular dystrophy, Becker muscular dystrophy, limb-girdle muscular dystrophy, or desmin myopathy, mitochondrial (mitochondrial respiratory gene defects) or metabolic disorders (severe anemia, thiamine deficiency), toxin-mediated (e.g., anthracycline) effects or related to congenital heart disease (coarctation of the aorta, anomalous origin of a coronary artery, critical aortic stenosis, large arteriovenous malformation).

The β1-selective adrenergic receptor antagonist may be selected from Nebivolol, CPG 20712A, ICI-89406, Practolol, Xamoterol, Bisoprolol, Betaxolol or Atenolol. The β1-adrenergic receptor-selective antagonist may be administered orally, transdermally, in sustained release, in controlled release, in delayed release, as a suppository, or sublingually. Alternatively, the β1-adrenergic receptor-selective antagonist may be administered intravenously, subcutaneously, or intraosseously.

The subject may be administered a second therapy for heart failure, such as an inotrope, a diuretic, ACE-I, Angiotensin-II antagonist, BNP, a $Ca^{++}$-blocker, or an HDAC inhibitor. Alternatively, the second therapy may be a β2-adrenergic receptor-selective agonist, such as albuterol (Albuterol, Ventolin), levoalbuterol, terbutaline (Bricanyl), pirbuterol (Maxair), procaterol, metaproterenol (Alupent), fenoterol, bitolterol mesylate, ritodrine, salmeterol (Serevent Diskus), formoterol (Foradil), bambuterol, clenbuterol, and indacaterol. The second therapy may be administered at the same time as said β1-adrenergic receptor-selective antagonist, or either before or after said β1-adrenergic receptor-selective antagonist.

The method may result in improvement of one or more signs or symptoms including, increased exercise capacity, increased cardiac ejection volume, decreased left ventricular end diastolic pressure, decreased pulmonary capillary wedge pressure, increased cardiac output, or cardiac index, lowered pulmonary artery pressures, decreased left ventricular end systolic and diastolic dimensions, decreased left and right ventricular wall stress, decreased wall tension, increased quality of life, and decreased disease-related morbidity or mortality.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 9A-B—Phospholamban phosphorylation at the serine 16 (Ser16) and threonine 17 (Thr17) sites in response to pathologic stimulation with isoproterenol (ISO) in old and young mice (n=10-14 animals/group). These sites correspond to the sites in human tissue in FIGS. 5A-C. The model recapitulated the age-dependent difference in humans in response to heart failure. Phosphorylation of both Ser16 and Thr17 was lower in the adult mouse heart under pathologic conditions (as previously demonstrated by others) but unchanged in the young mouse hearts of the model. These data demonstrate the human age-specific adrenergic molecular mechanisms are recapitulated in the mouse model. *P<0.0001

DETAILED DESCRIPTION OF ILLUSTRATIVE EMBODIMENTS

Figure 1A:
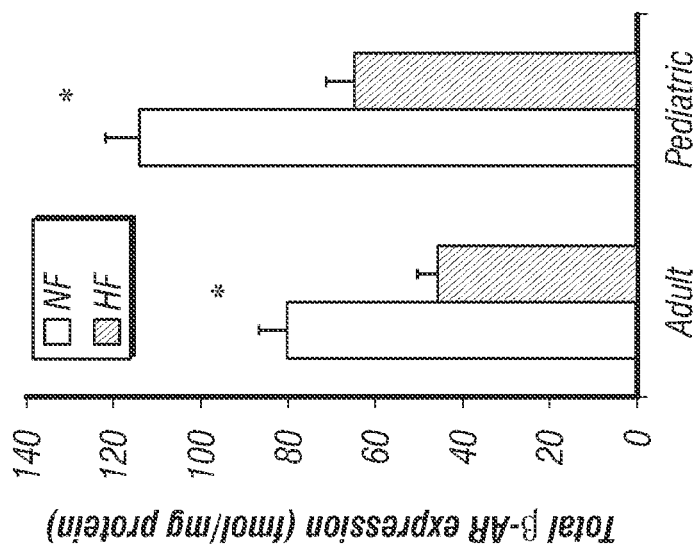
FIGS. 1A-C—Beta-adrenergic receptor (β-AR) protein binding assays performed on failing and non-failing left ventricle from children and adults. Total (FIG. 1A) and subtype specific (FIGS. 1B and 1C) β-AR expression in adult and pediatric failing and nonfailing left ventricle. Heart failure downregulates the β-AR in both children and adults. In adults, the decrease in total β-AR is due to a significant decline in β1-AR without significant change in β2-AR. In contrast, both β-AR subtypes are downregulated by pediatric heart failure.

Heart failure is one of the leading causes of morbidity and mortality in the world. In the U.S. alone, estimates indicate that 3 million people are currently living with cardiomyopathy and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Approximately half of the DCM cases are idiopathic, with the remainder being associated with known disease processes. For example, serious myocardial damage can result from certain drugs used in cancer chemotherapy (e.g., doxorubicin and daunoribucin). In addition, many adult DCM patients are chronic alcoholics. Fortunately, for these patients, the progression of myocardial dysfunction may be stopped or reversed if alcohol consumption is reduced or stopped early in the course of disease. Peripartum cardiomyopathy is another form of DCM, as is disease associated with infectious sequelae. In sum, cardiomyopathies, including idiopathic DCM, are significant public health problems. In the United States, approximately half a million individuals are diagnosed with heart failure each year, with a mortality rate approaching 50%. The cost to diagnose, treat and support patients suffering from these diseases is well into the billions of dollars.

The etiology of heart failure in children is different from that in adults; therefore, it is erroneous to assume that response to clinical therapy in children will be identical to that demonstrated in adults. Similar to adults, idiopathic dilated cardiomyopathy is one of the most prevelant causes of heart failure in children. However, the causes of DCM in children are different from adults, with a much higher incidence of infectious myocarditis, familial and genetic diseases. In contrast to the adult population, there is virtually no ischemic heart disease in children and a very high prevalence of congenital heart disease in the heart failure population. It is important to note that due to the anatomical heterogeneity of the pediatric heart failure population, references to ventricular function usually specify systemic versus non-systemic ventricle instead of references to right and left ventricular function as in the adult population. Although the annual incidence of cardiomyopathies in children is lower than in adults (1 per 100,000 in children vs 4-5 per 100,000 individuals in adults), the severity of disease is equally devastating, with 1- and 5-year rates of death or transplantation of 30% and 40% respectively.

Regardless of age, heart failure is associated with elevated blood catecholamines. For example, norepinephrine levels are similar in children and adults with heart failure. Catecholamines activate β-adrenergic receptors in the heart and cause changes in expression and activation of both the β1 and β2 receptor subtypes. Given the lack of clinical benefit of carvedilol therapy in children with heart failure, the inventors hypothesized that there are critical differences in β-adrenergic receptor remodeling in response to heart failure between adults and children. To address this hypothesis, they determined β-adrenergic receptor mRNA and protein expression in non-failing and failing left ventricular samples from children and adults. Consistent with previously published data, they found a downregulation of total β-adrenergic receptors in the failing adult heart that is primarily due to selective downregulation of the β1 receptor. There is no change in β2 receptor expression in the adult heart. The inventors also found that total β receptor number decreased in the failing pediatric heart due to downregulation of both β1 and β2 subtypes. This profile is unique to the pediatric population and, as explained below, may underlie the lack of clinical benefit in the Pediatric Carvedilol Trial mentioned above. Thus, the inventors propose to selectively inhibit β1 receptors in the treatment of pediatric heart failure patients. This and other aspects of the invention are described in greater detail below.

I. β-ADRENERGIC RECEPTORS

The adrenergic receptors (or adrenoceptors) are a class of G protein-coupled receptors that are targets of the catecholamines, especially noradrenaline (norepinephrine) and adrenaline (epinephrine). Although dopamine is a catecholamine, its receptors are in a different category. Many cells possess these receptors, and the binding of an agonist will generally cause a sympathetic response (e.g., the fight-or-flight response). For instance, the heart rate will increase and the pupils will dilate, energy will be mobilized, and blood flow diverted from other non-essential organs to skeletal muscle.

There are two main groups of adrenergic receptors, α and β, with several subtypes. α receptors have the subtypes $β_1$ (a $G_q$ coupled receptor) and $α_2$ (a $G_i$ coupled receptor). Phenylephrine is a selective agonist of the α1 receptor. β receptors have the subtypes $β_1$, $β_2$ and $β_3$. All three are linked to $G_s$ proteins (although $β_2$ also couples to Gi), which in turn are linked to adenylate cyclase. Agonist binding thus causes a rise in the intracellular concentration of the second messenger cAMP (cyclic adenosine monophosphate). Downstream effectors of cAMP include cAMP-dependent protein kinase (PKA), which mediates some of the intracellular events following hormone binding. Isoprenaline/isoproterenol is a non-selective agonist of the β-receptors.

The β-1 adrenergic receptor is a G-protein coupled receptor associated with the Gs heterotrimeric G-protein. Specific polymorphisms in this gene have been shown to affect the resting heart rate and can be involved in heart failure. β-1 adrenergic receptor has been shown to interact with DLG4 and GIPC1.

The β-2 adrenergic receptor is directly associated with one of its ultimate effectors, the class C L-type calcium channel $Ca_v1.2$. This receptor-channel complex is coupled to the $G_s$ G protein, which activates adenylyl cyclase, catalysing the formation of cyclic adenosine monophosphate (cAMP) which then activates protein kinase A, and the counterbalancing phosphatase PP2A. The assembly of the signaling complex provides a mechanism that ensures specific and rapid signaling. β-2 receptors have also been found to couple with $G_i$, possibly providing a mechanism by which response to ligand is highly localized within cells. Importantly, this Gi mediated pathway is now believed to be a beneficial and pro-survival pathway. In contrast, β-1 receptors are coupled only to $G_s$, and stimulation of these results in a more diffuse cellular response. This appears to be mediated by cAMP induced PKA phosphorylation of the receptor.

A. β-1 Subtype Selective Receptor Antagonists

In one aspect of the present invention, the methods will involve the use of β1-selective antagonists, which are well known. These include, but are not limited to Acebutolol, Atenolol, Betaxolol, Bisoprolol, Esmolol, Metoprolol, and Nebivolol. In a particular aspect, the antagonist will have a specific level of selectivity, such as having a selectivity greater than that of Metoprolol, or multiples of the selectivity of Metoprolol, such as 2-, 3-, 4-, 5-, 6-, 7-, 8-, 9-, 10-, 15-, 20-, 50- or 100-times that of Metoprolol.

TABLE 1

| Drug | Pediatric Indication | How supplied | Dose |
| --- | --- | --- | --- |
| Acebutolol | None | Oral capsule | No peds dosing available |
| Atenolol | Cardiac dysrhythmia, hypertension | Tablet | Dysrhythmia: 0.3-1.4 mg/kg once daily, max 2 mg/kg/day Hypertension: 0.5-1 mg/kg/day divided |

TABLE 1-continued

| Drug | Pediatric Indication | How supplied | Dose |
|---|---|---|---|
| | | | 1-2 times daily, max 2 mg/kg/day up to 100 mg/day |
| Betaxolol | Glaucoma | Ophthalmic solution, tablet | No peds dosing available |
| Bisoprolol | None | Tablet | No peds dosing available |
| Esmolol | None | IV only | |
| Metoprolol | Hypertension | Tablet | >6 years: 1 mg/kg once daily, max 50 mg daily |
| Nebivolol | None | Tablet | No peds dosing available |

B. β-2 Subtype Receptor Agonists

In another aspect of the present invention, the methods will involve the use of β2-selective agonists in combination with β1-blockade, discussed above. Such agonists include, but are not limited to, salbutamol, bitolterol mesylate, isoproterenol, levalbuterol, metaproterenol, salmeterol, terbutaline, clenbuterol, or ritodrine.

TABLE 2

| Drug | Pediatric Indication | How supplied | Dose |
|---|---|---|---|
| Salbutamol | Asthma | Tablet and syrup | Age 2-6 years: 0.1-0.2 mg/kg/dose TID up to 4 mg TID<br>Age 6-12 years: 2-6 mg TID or QID<br>Age >12 years: 2-8 mg TID or QID |
| Bitolterol mesylate (no longer available in US) | Asthma/ Bronchospasm | No oral prep (MDI or nebulizer) | |
| Isoproterenol | Asthma | Sublingual | 5-10 mg up to 3 times daily, max dose 30 mg/day |
| Levalbuterol | Asthma | No oral prep (Inhalation solution) | |
| Metaproterenol | Asthma/ Bronchospasm | Tablet and syrup | <2 years: 0.4 mg/kg Q8-Q12 hours<br>2-6 years: 1.3-2.6 mg/kg/day divided into 3-4 doses<br>6-9 years: 10 mg 3-4 times daily<br>>9 years: 20 mg 3-4 times daily |
| Salmeterol | Asthma | No oral prep (Inhalation solution) | |
| Terbutaline | Bronchospasm | Tablet | 12-15 years: 2.5 mg TID |
| Clenbuterol | Asthma | Oral prep | 5-13 years: single dose of 0.5-1.5 mcg/kg/dose |
| Ritodrine | Pre-term labor | Tablet | No peds dosing available |

II. METHODS OF TREATING HEART FAILURE

A. Therapeutic Regimens

Current medical management of cardiac failure in the setting of a cardiovascular disorder includes the use of at least two types of drugs: inhibitors of the renin-angiotensin system, and β-adrenergic blocking agents (Eichhorn and Bristow, 1996 and Bristow, 1999). Other pharmaceutical agents that have been disclosed for treatment of heart failure include angiotensin II receptor antagonists (U.S. Pat. No. 5,604,251) and neuropeptide γ antagonists (WO 98/33791). Despite currently available pharmaceutical compounds, prevention and treatment of cardiac hypertrophy, and subsequent heart failure, continue to present a therapeutic challenge.

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids). Surgical intervention may also be contemplated.

Thus, in one aspect of the present invention, methods for the treatment of heart failure utilizing β1-selective antagonists are provided. For the purposes of the present application, treatment comprises improving one or more of the signs or symptoms of heart failure, such as reduced exercise capacity, reduced blood ejection volume, increased left ventricular end diastolic pressure, increased pulmonary capillary wedge pressure, reduced cardiac output, cardiac index, increased pulmonary artery pressures, increased left ventricular end systolic and diastolic dimensions, and increased left ventricular wall stress, wall tension and wall thickness-same for right ventricle.

Treatment regimens would vary depending on the clinical situation. However, long term maintenance would appear to be appropriate in most circumstances. It also may be desirable to treat patients with β1-selective antagonists intermittently, such as within a brief window during disease progression.

B. Combined Therapy

In another embodiment, it is envisioned to use a β2-selective agonist in combination with other therapeutic modalities. Thus, in addition to the therapies described above, one may also provide to the patient more "standard" pharmaceutical cardiac therapies. Examples of other therapies include, without limitation, anti-hypertensives, cardiotonics, anti-thrombotics, vasodilators, hormone antagonists, inotropes, diuretics, endothelin antagonists, calcium channel blockers, phosphodiesterase inhibitors, ACE inhibitors, angiotensin receptor type 2 antagonists and cytokine blockers/inhibitors, and HDAC inhibitors. A particular form of combination therapy will include the use of β2-selective agonists. This combination is designed to take advantage of the differential β-adrenergic receptor expression changes unique to pediatric heart failure subjects.

Combinations may be achieved by contacting cardiac cells with (i.e., administering to patients) a single composition or pharmacological formulation that includes both agents, or by contacting the cell with two distinct compositions or formulations, at the same time, wherein one composition includes the expression construct and the other includes the agent. Alternatively, the therapy using a β2-selective agonist may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a β2-selective agonist, or the other agent will be desired. In this regard, various combinations may be employed. By way of illustration, where the β2-selective agonist is "A" and the other agent is "B," the following permutations based on 3 and 4 total administrations are exemplary:

| | | | | | |
|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof. Other combinations are likewise contemplated. Some specific agents are described below.

i. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol), simvastatin (zocor), atorvastatin (Lipitor) or rosuvastatin (crestor).

d. Nicotinic Acid Derivatives

Non-limiting examples of nicotinic acid derivatives include nicotinate, acepimox, niceritrol, nicoclonate, nicomol and oxiniacic acid.

e. Thyroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5, 8, 11, 14, 17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

ii. Antiarteriosclerotics

Non-limiting examples of an antiarteriosclerotic include pyridinol carbamate.

iii. Antithrombotic/Fibrinolytic Agents

In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantine), heparin, sulfinpyranone (anturane), ticlopidine (ticlid), clopidigrel (Plavix) and ticagrelor (Brilinta).

c. Thrombolytic Agents

Non-limiting examples of thrombolytic agents include tissue plaminogen activator (activase), plasmin, pro-urokinase, urokinase (abbokinase) streptokinase (streptase), anistreplase/APSAC (eminase).

iv. Blood Coagulants

In certain embodiments wherein a patient is suffering from a hemorrhage or an increased likelihood of hemorrhaging, an agent that may enhance blood coagulation may be used. Non-limiting examples of a blood coagulation promoting agent include thrombolytic agent antagonists and anticoagulant antagonists.

a. Anticoagulant Antagonists

Non-limiting examples of anticoagulant antagonists include protamine and vitamin K.

b. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

v. Antiarrhythmic Agents

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrythmic agents (calcium channel blockers) and miscellaneous antiarrythmic agents.

a. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and flecainide (tambocor).

b. Repolarization Prolonging Agents

Non-limiting examples of an agent that prolong repolarization, also known as a Class III antiarrhythmic agent, include amiodarone (cordarone) and sotalol (betapace).

c. Calcium Channel Blockers/Antagonist

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a miscellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

d. Miscellaneous Antiarrhythmic Agents

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

vi. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an α-adrenergic blocker or an α-adrenergic antagonist, include, amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

e. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimethylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten).

Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives.

Non-limiting examples of arylethanolamine derivatives include amosulalol, bufuralol, dilevalol, labetalol, pronethalol, sotalol and sulfinalol.

Benzothiadiazine Derivatives.

Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

N-Carboxyalkyl(Peptide/Lactam) Derivatives.

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives.

Non-limiting examples of dihydropyridine derivatives include amlodipine, felodipine, isradipine, nicardipine, nifedipine, nilvadipine, nisoldipine and nitrendipine.

Guanidine Derivatives.

Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines.

Non-limiting examples of hydrazines/phthalazines include budralazine, cadralazine, dihydralazine, endralazine, hydracarbazine, hydralazine, pheniprazine, pildralazine and todralazine.

Imidazole Derivatives.

Non-limiting examples of imidazole derivatives include clonidine, lofexidine, phentolamine, tiamenidine and tolonidine.

Quanternary Ammonium Compounds.

Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives.

Non-limiting examples of reserpine derivatives include bietaserpine, deserpidine, rescinnamine, reserpine and syrosingopine.

Suflonamide Derivatives.

Non-limiting examples of sulfonamide derivatives include ambuside, clopamide, furosemide, indapamide, quinethazone, tripamide and xipamide.

g. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

vii. Treatment Agents for Congestive Heart Failure

Non-limiting examples of agents for the treatment of congestive heart failure include anti-angiotension II agents, afterload-preload reduction treatment, diuretics and inotropic agents.

a. Afterload-Preload Reduction

In certain embodiments, an animal patient that can not tolerate an angiotension antagonist may be treated with a combination therapy. Such therapy may combine administration of hydralazine (apresoline) and isosorbide dinitrate (isordil, sorbitrate).

b. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

c. Inotropic Agents

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

d. Antianginal Agents

Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

C. Surgical Therapeutic Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise extracorporeal membrane oxygenation (ECMO), an intra-aortic balloon counterpulsation, left (or bi-) ventricular assist device or combination thereof.

D. Drug Formulations and Routes for Administration to Patients

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render drugs stable and allow for uptake by target cells. Aqueous compositions of the present invention comprise an effective amount of the drug, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes is administered orally, nasally, bucally, transdermally, in sustained release, in controlled release, in delayed release, as a suppository, sublingually, intravenously, subcutaneously, or intraosseously. Alternatively, administration may be by intradermal, intramuscular, or intraperitoneal, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

III. DEFINITIONS

As used herein, the term "heart failure" is broadly used to mean any condition that reduces the ability of the heart to pump blood. As a result, congestion and edema develop in the tissues. Many factors may result in heart failure, including reduced coronary blood flow, damage to the heart valves, congenital abnormalities, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The term "treatment" or grammatical equivalents encompasses modalities aimed at improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, heart size, left ventricular internal dimension, heart rate, etc.), as well as any effect upon the animal's survival. In use of animal models, the response of treated animals and untreated animals is compared using any of the assays described herein. A compound which causes an improvement in any parameter associated with heart failure used in the screening methods of the instant invention may thereby be identified as a therapeutic compound.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the term "agonist" refers to molecules or compounds which mimic the action of a "native" or "natural" compound. Agonists may be homologous to these natural compounds in respect to conformation, charge or other characteristics. Thus, agonists may be recognized by receptors expressed on cell surfaces. This recognition may result in physiologic and/or biochemical changes within the cell, such that the cell reacts to the presence of the agonist in the same manner as if the natural compound was present. Agonists may include proteins, nucleic acids, carbohydrates, or any other molecules that interact with a molecule, receptor, and/or pathway of interest.

As used herein, the terms "antagonist" and "inhibitor" refer to molecules, compounds, or nucleic acids which inhibit the action of a cellular factor that may be involved in cardiac hypertrophy or failure. Antagonists may or may not be homologous to these natural compounds in respect to conformation, charge or other characteristics. Thus, antagonists may be recognized by the same or different receptors that are recognized by an agonist. Antagonists may have allosteric effects which prevent the action of an agonist. Antagonists and inhibitors may include proteins, nucleic acids, carbohydrates, or any other molecules which bind or interact with a receptor, molecule, and/or pathway of interest.

As used herein, the term "modulate" refers to a change or an alteration in a biological activity. Modulation may be an increase or a decrease in protein activity, a change in kinase activity, a change in binding characteristics, or any other change in the biological, functional, or immunological properties associated with the activity of a protein or other structure of interest. The term "modulator" refers to any molecule or compound which is capable of changing or altering biological activity as described above.

The term "β-adrenergic receptor antagonist" refers to a chemical compound or entity that is capable of blocking, either partially or completely, the beta (β) type of adrenoreceptors (i.e., receptors of the adrenergic system that respond to catecholamines, especially norepinephrine). Some β-adrenergic receptor antagonists exhibit a degree of specificity for one receptor sybtype, and such antagonists are termed "β1-selective adrenergic receptor antagonists" and "β2-selective adrenergic receptor antagonists." The term "β-adrenergic receptor antagonist" refers to chemical compounds that are selective and non-selective antagonists. Examples of β-adrenergic receptor antagonists include, but are not limited to, acebutolol, atenolol, butoxamine, carteolol, esmolol, labetolol, metoprolol, nadolol, penbutolol, propanolol, bisoprolol, nebivolol and timolol. The use of derivatives of known β-adrenergic receptor antagonists is encompassed by the methods of the present invention. Indeed any compound, which functionally behaves as a β-adrenergic receptor antagonist is encompassed by the methods of the present invention.

IV. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Tissue Procurement.

Explanted human ventricular tissue from Nonfailing (NF) human hearts were obtained from unused organ donors with no history of cardiac dysfunction (left ventricular ejection fractions 65%±9 by echocardiograms performed as part of the organ recovery process) or coronary artery disease. Failing hearts were obtained from cardiac transplant recipients with advanced nonischemic idiopathic dilated cardiomyopathies (IDC). Mean age for adults was 49±2 and for children it was 9±1 years. Human subjects were males and females of all ages, races and ethnic background who donated their heart to the institutional review board-approved adult and pediatric transplant tissue banks at the University of Colorado. All failing samples (adult and pediatric) have left ventricle ejection fraction of <30%. At the time of cardiac transplantation, the explanted hearts were immediately cooled in ice cold oxygenated Tyrodes in the operating room. The LV was rapidly dissected, flash frozen and stored at −80° C. until further use.

β-Adrenergic Receptor Protein Expression.

Protein was isolated from pediatric (15 failing and 15 nonfailing) and adult (9 failing and 11 nonfailing) human explanted failing and non-transplanted donor left ventricle (LV) in cold 20 mM Tris, 1 mM EGTA, pH 7.5. All samples were extensively washed (3 washes in 20 mM Tris, 150 mM NaCl and 1 mM ascorbate at pH 7.8 at 4° C.) to remove any therapeutically administered β-blockers (Lowes et al., 2002). Total βAR density and β1 and β2AR subtype expression was determined using a 9-point 15 saturation curve of increasing concentrations of $^{125}$I-iodocyanopindolol (ICYP) and computer modeling of 17-19 point betaxolol-ICYP competition curves, respectively, as previously described (Bristow et al., 1984; Bristow et al., 1986; Lowes et al., 1997; Brodde et al., 1991).

Antibodies.

Phospholamban Ser16 (A010-12) and Thr17 (A010-13) antibodies were purchased from Badrilla. The total phospholamban antibody was purchased from Millipore. Total Akt (protein kinase B) and caspase 3 antibodies were purchased from Cell Signaling. The phosphorylated Akt antibody was purchased from GenScript (A00272). Calnexin antibody was purchased from Abcam (AB 13504) and GAPDH antibody was purchased from Santa Cruz Biotechnology (sc-20357). The HRP (115-035-146) anti-mouse and anti-rabbit were purchased from Jackson Laboratories.

Real Time PCR.

Total RNA was extracted by mirVana™ kit (Ambion). 0.5 µg of RNA were reverse transcribed into cDNA using I-script (Bio-Rad). Typically, 0.1 ng of cDNA, 12.5 nM of each primer and Power Syber Green PCR Master Mix (ABI) were used in the RT-PCR reactions. Reactions were performed using the ABI7300 system. The primers have been previously described (Sucharov et al., 2008) or are listed below:

```
Connexin43 (Cx43)
                                       (SEQ ID NO: 1)
F-5'AGTTCAATCACTTGGCGTGACTTCACTA Cx43
                                       (SEQ ID NO: 2)
R-5'CCTGGGCACTCTTTTGCTTA BNP
                                       (SEQ ID NO: 3)
F-5'GGTGCTGCCCCAGATGATT BNP
                                       (SEQ ID NO: 4)
R-5'CTGGAGACTGGCTAGGACTTC αMyHC
                                       (SEQ ID NO: 5)
F-5'CCTGTCCAGCAGAAAGAGC αMyHC
                                       (SEQ ID NO: 6)
R-5'CAGGCAAAGTCAAGCATTCATATTTATTGTG βMyHC
                                       (SEQ ID NO: 7)
F-5'CGCTCAGTCATGGCGGAT βMyHC
                                       (SEQ ID NO: 8)
R-5'GCCCCAAATGCAGCCAT SERCA
                                       (SEQ ID NO: 9)
F-5'GGCCAGATCGCGCTACA SERCA
                                       (SEQ ID NO: 10)
R-5'GGGCCAATTAGAGAGCAGGTTT ANP
                                       (SEQ ID NO: 11)
F-5'GCGAAGGTCAAGCTGCTT ANP
                                       (SEQ ID NO: 12)
R-5'CTGGGCTCCAATCCTGTCAAT β₁-AR
                                       (SEQ ID NO: 13)
F-5'GGGCATCATCATGGGCGTCTT β₁-AR
                                       (SEQ ID NO: 14)
R-5'TTCACCACGTTGGCCAGGAAG
```

-continued

β₂-AR
F-5'CAAGTACCAGAGCCTGCTGACCAA (SEQ ID NO: 15)

β₂-AR
R-5'GGAGGTAAGGCCTGACACAATCCA (SEQ ID NO: 16)

Western Blots.

Western blots were performed as previously described by the inventors [2]. Antibodies for total and phosphorylated PLB were diluted 1:15000 and antibodies for total and phosphorylated Akt were diluted 1:1000 in 1×TBS (20 mM Tris 500 mM NaCl pH 7.5) containing 3% BSA and 0.1% tween and incubated with the blot overnight at 4° C.

cAMP Assay.

Left ventricle tissue was homogenized by Polytron (Model PT 1200E) on ice for 2×10 seconds in 10 volumes of 1× Cell Lysis 5 Buffer from the Parameter Cyclic AMP Assay Kit (KGE002) from R&D Systems. The homogenate was centrifuged at 4° C. for five minutes at 20,800×g. The supernatants were extracted and snap frozen in liquid nitrogen and stored at −80° C. Protein assays were performed on the supernatants using the Pierce BCA Protein Assay (23225). ELISA was performed by the CCTSI core facility at Children's Hospital Colorado, Aurora, Colo.

CaMK Activity Assay.

Nuclear and cytoplasmic protein fractions were prepared from frozen left ventricular tissue using the NE-PER kit (Thermo Scientific, Rockford, Ill.). CaMK activity was measured as described by Kirchhefer et al. (1999). Briefly, 5 μg of protein were combined with 20 μM Syntide 2 (Bachem, Torrance, Calif.) and 5 μCi [α-$^{32}$P] ATP. Total protein kinase activity was measured in the presence of 1 μM CaCl$_2$ and 10 μg/ml calmodulin, and Ca$^{2+}$-independent protein kinase activity was determined by the addition of 5 mM EGTA. CaMK activity was expressed as incorporation of pmoles $^{32}$P per mg protein per minute.

MicroRNA Extraction and Array Analysis.

miRNA was extracted from 5 non-failing and 5 idiopathic dilated cardiomyopathy pediatric hearts and 6 non-failing and 5 idiopathic dilated cardiomyopathy adult hearts. miRNA extraction was performed using the mirVana™ kit (Ambion) according to manufacturer's recommendation. miRNA expression analysis was performed by LC Science, LLC (Houston, Tex.) using arrays based on the Sanger miRBase 14.0 database, (world-wide-web at sanger.ac.uk/Software/Rfam/mirna/), capable of detecting 894 miRNAs.

Mouse Model of Pediatric Heart Failure.

Figure 8:
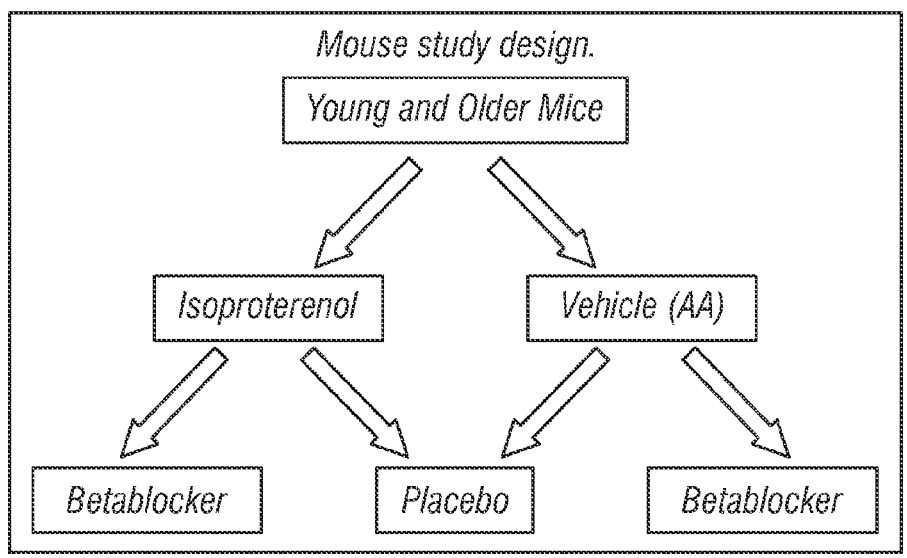
FIG. 8—Mouse intervention study design.

The inventors performed in vivo studies in prepubescent and older mice to test their hypotheses that (i) β1-selective blockers demonstrate benefit, (ii) non-selective adrenergic receptor antagonist are not beneficial in children, but (iii) both are beneficial in adults and the hypothesis (iv) that β2-selective agonism is beneficial in children. Since a primary characteristic of human heart failure is endogenous catecholamine (epinephrine and norepinephrine; full β1 and β2 receptor agonists) excess, they challenged the mice with isoproterenol (an exogeous full β1 and β2 receptor agonist) for 7 days using a subcutaneous miniosmotic pump at a dose (30 mg/kg/day) that has previously been associated with cardiac hypertrophy in adult mice and has been used as a model of cardiac hypertrophy and heart failure in adult humans. Higher doses (120 mg/kg/day) for 14 days cause a dilated heart failure phenotype, providing further evidence that this is an appropriate HF model. Half the animals received the isoproterenol treatment and the other half were treated with placebo pumps filled with normal saline and vitamin C, the vehicle that the isoproterenol is dissolved in. The young and old animals were divided into 2 studies: one for carvedilol treatment and one for metoprolol treatment (the study design for each animal study is illustrated in FIG. 8). Within each study, animals were either given plain water or the β-blocker suspended in the drinking water at doses previously demonstrated to be efficacious (Bartholomeu et al., 2008; Harding et al., 2001). The amount of water consumed was measured on a daily basis and all groups consumed similar amounts of water. In a second study to further support hypothesis (i) above and provide evidence of a class effect among β1-selective antagonists, young mice were divided into 2 studies one for bisoprolol and one for nebivolol. Within each study the β-blocker or the vehicle (the compound the β-blocker was dissolved in, as outlined above) was administered via a subcutaneously implanted pump at doses previously demonstrated to be efficacious (Dalla Libera et al., 2010; Whaley-Connell et al., 2009) [6, 7]. After 7 days of treatment, the hearts were removed and assessed for cardiac growth in response to isoproterenol with or without the β-blocker. Protein was isolated from the hearts of young and old mice in the presence or absence of isopretrenol without any β-blocker treatment assessed for phosphorylation of phospholamban by Western blot as outlined above.

To address hypothesis (iv) above a third study was performed in the young mice to provide evidence of the beneficial effects of exogenous β2-selective agonism with fenoterol. Young mice were treated with isoproterenol or placebo pumps as outlined above or with fenoterol administered in the drinking water at a dose previously demonstrated to be efficacious in adult rats (Ahmet et al., 2004; 2005; 2008). The methodology was identical to that outlined in the carvedilol and metoprolol studies above. Protein was isolated from the placebo, fenoterol and isoproterenol treated mouse hearts and phosphorylation of Akt and expression of Caspase 3 was determined to confirm the beneficial effects of fenoterol treatment.

Statistical Analysis.

Statistical analyses were performed using Statview software (SAS Institute, Cary, N.C.). Disease and age comparisons were performed by Student's t-Test for all experimental outcomes. 2-way Analysis of Variance (ANOVA) was performed including all groups to evaluate for interactions. Statistical significance was set a priori at $P<0.05$.

Example 2

Results

Figure 1B:
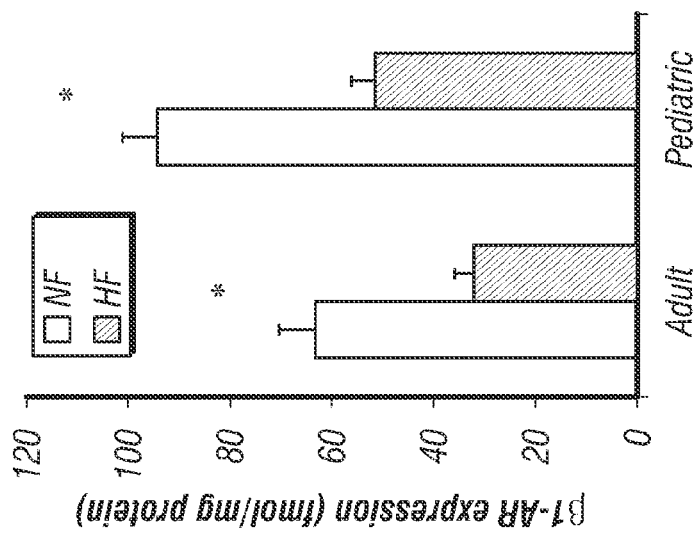
Figure 1C:
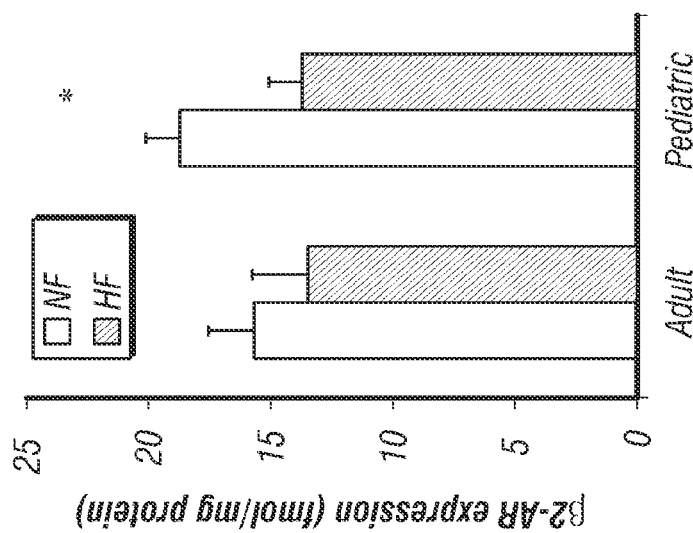

Age-related changes in β-adrenergic receptor (AR) expression due to heart failure in humans were included in the provisional application and can be summarized as isolated β1 receptor down-regulation in adults and both β1 and β2 receptor down-regulation in children (FIGS. 1A-C). The inventors subsequently evaluated several of the molecular pathways downstream from the β receptors. To demonstrate that any age-related differences found were not due to experiment technique alone, the inventors performed the experimental evaluations in both pediatric and adult failing and non-failing tissue. The inventors have recapitulated the known adult abnormalities in CaMK activity, cAMP levels, phosphorylation of PLB at 2 sites, and gene expression of beta receptors and a pathologic gene program in response to heart failure. The failing pediatric heart shows differences in response to heart failure in all these areas when compared to their adult counterparts.

Although there are remarkable differences in total βAR number between human adults and children under normal conditions, the total βAR number (fmol/mg protein) is significantly lower in both the pediatric and adult failing ventricle (FIG. 1A). However, changes in the number of each receptor subtype (β1 and β2 receptor) are different in the children than adults due to heart failure (FIGS. 1B and 1C). In adults, the number of β1 receptors is lower in the failing hearts without any change in the number of β2 receptors. In contrast, in children both the β1 and β2 receptors are lower in the failing heart. Thus, the normal β1:β2 receptor ratio (~80%:20%) only has a minor change in the pediatric HF samples, which is 25 to 50% of the change in the β1:β2 ratio in adults with heart failure noted by the inventors' group and others (Lowes et al., 2002; Milting et al., 2006). These data demonstrate a unique β2 receptor downregulation with heart failure in children. Since the β2 receptor is responsible for many of the beneficial effects of catecholamines, blocking this downregulated receptor in children, as was done in the Pediatric Carvedilol Trial, is likely detrimental and responsible for the lack of benefit due to significantly lower signaling through this pathway. In contrast, adults with preserved β2 receptor number in heart failure have a sufficient amount of the receptor to be able to tolerate some β2 receptor blockade, as with carvedilol, and reap the beneficial effects of β1 receptor blockade as seen with both carvedilol and metoprolol succinate.

Figure 2:
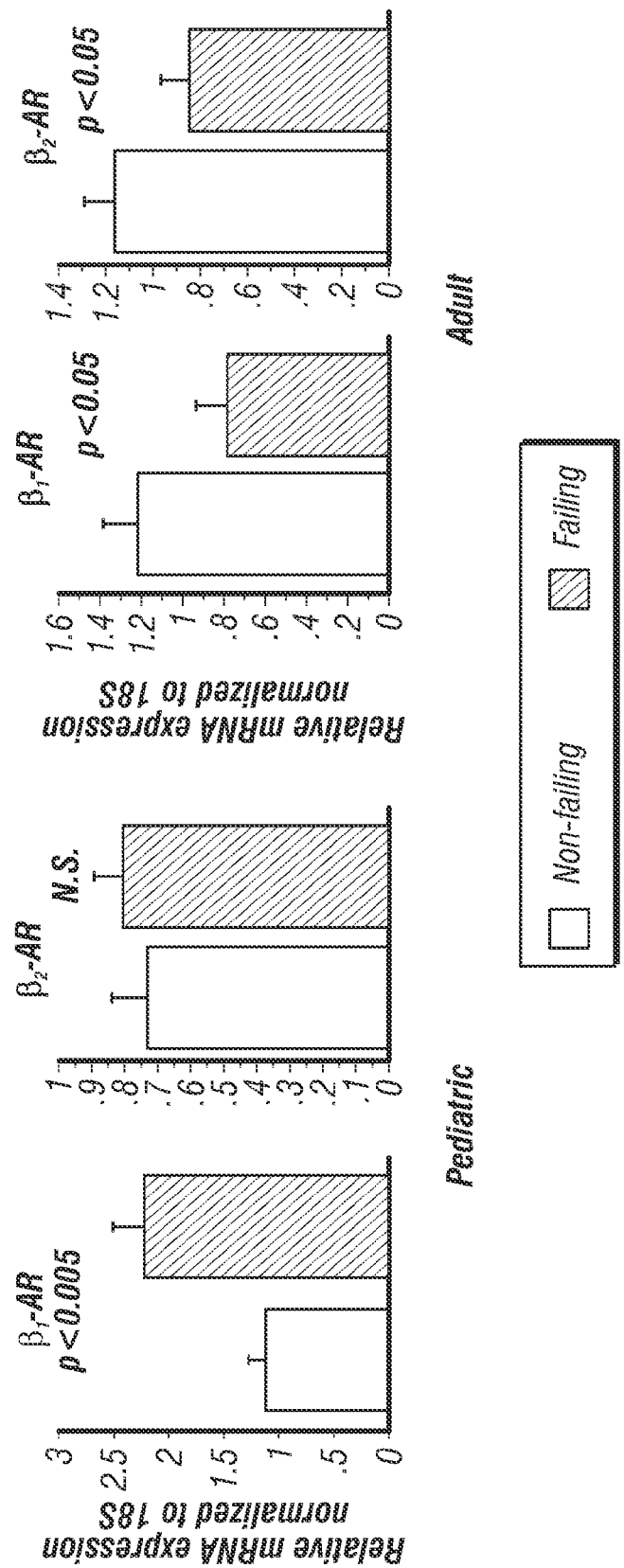
FIG. 2—Antithetical regulation of $β_1$-AR and $β_2$-AR mRNA levels in pediatric and adult heart failure (HF) patients. mRNA levels were determined by RT-PCR. p values correspond to failing (F) to non-failing (NF) comparisons. (N=37 NF pediatric, 52 F pediatric, 26 NF adults, 22 F adults).
Figure 3:
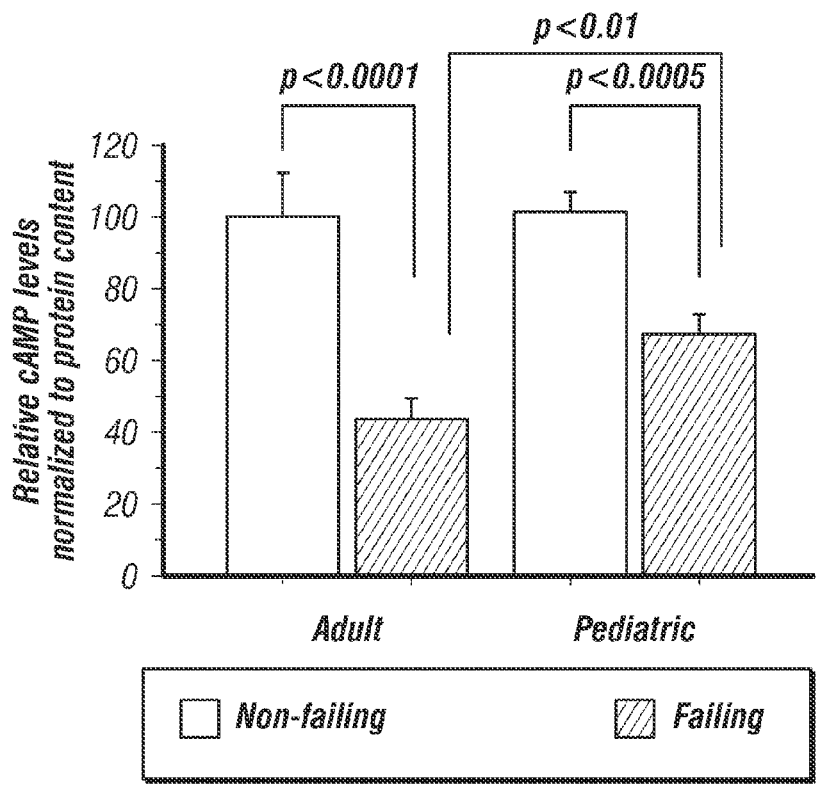
FIG. 3—Down-regulation of cyclic adenosine monophosphate (cAMP) levels is greater in adult than in pediatric heart failure patients. cAMP levels were measure by ELISA. (N=22 NF pediatric, 27 F pediatric, 6 NF adults, 16 F adults).

To follow-up the age-related differences in β receptor expression at the protein level, the inventors performed real-time quantitative PCR on heart extracts. FIG. 2 shows that β receptor mRNA expression demonstrates unique age-related characteristics and suggests unique transcriptional regulation between adults and children in response to heart failure. In adults, β1-AR transcript number is increased and the β2-AR transcript is not changed in response to heart failure. In contrast, in children both β1 and β2-AR mRNA levels are decreased in the failing heart. The classic β1 intracellular pathway results in activation of adenylate cyclase and the production of cAMP, an important second messenger that activates protein kinase A (PKA) which is the terminal effector of this cascade. Down-regulation and uncoupling of the beta1 receptor in response to heart failure produces a decrease in intracellular cAMP in adults (FIG. 3 and others (Bristow et al., 1992)). Although cAMP levels are significantly lower in the failing pediatric heart than non-failing controls the levels are higher than those in the failing adult heart (FIG. 3).

Figure 4:
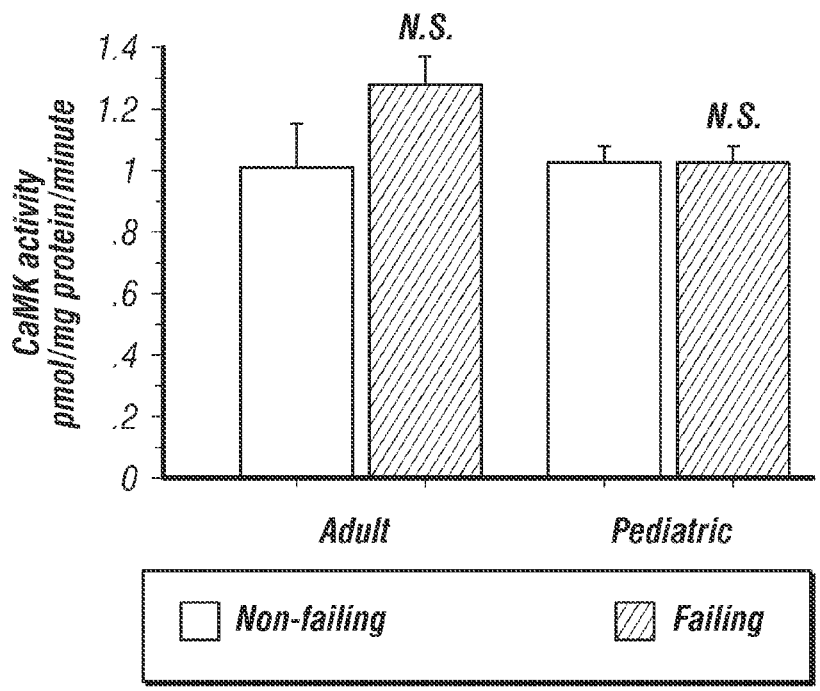
FIG. 4—Calcium-calmodulin kinase (CaMK) activity does not change in pediatric heart failure patients. CaMK activity was determined in 10 NF pediatric, 10 F pediatric, 4 NF adult and 4 F adult subjects.

The second major signaling cascade downstream from the beta1 receptor results in activation of Calcium-calmodulin kinase (CaMK). CaMK is known to be activated with heart failure and is responsible for many of the pathologic features of heart failure in adults (FIG. 4 and others (Dalla Libera et al., 2010). In contrast, there is no activation of CaMK in response to heart failure in children (FIG. 4). These data indicate that a major pathologic mediator of heart failure in adults is not activated in children in response to heart failure and suggest that the mechanism(s) of disease are distinctly different between children and adults.

Figure 5A:
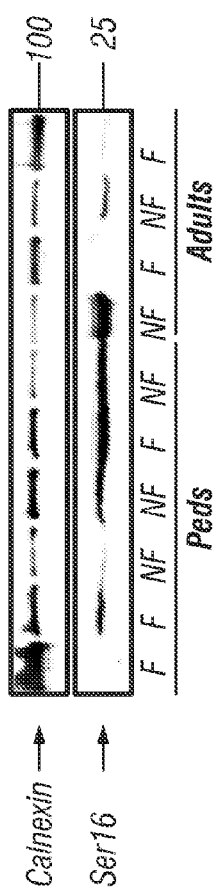
FIGS. 5A-C—Phosphorylated phospholamban (P-PLB) levels are down-regulated in adult (as previously demonstrated by multiple groups) but not in pediatric heart failure patients. Serine 16 (Ser16, FIG. 5A) and threonine 17 (Thr17, FIG. 5B) phosphorylation levels and total PLB (FIG. 5C) level were measured by Western blot and normalized to calnexin.
Figure 5A:
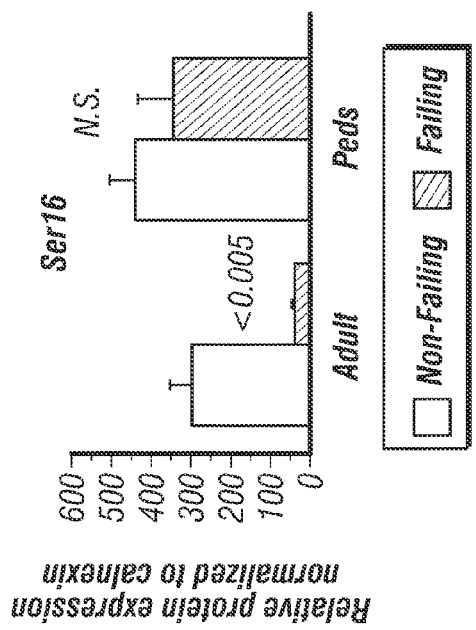
Figure 5B:
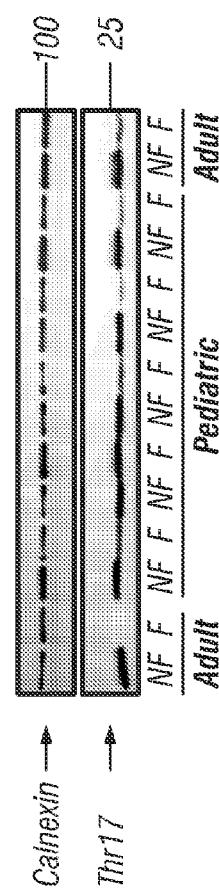
Figure 5B:
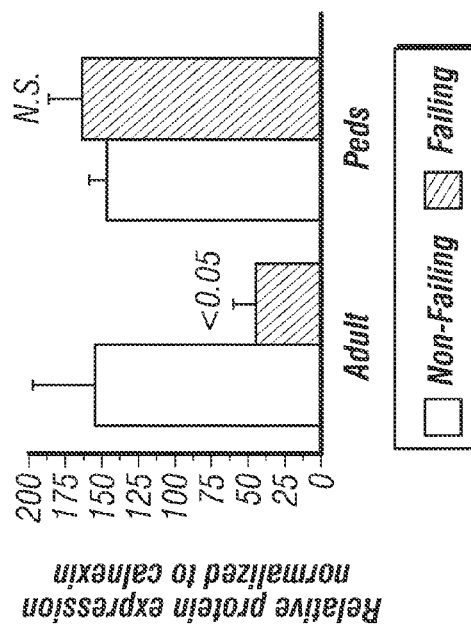
Figure 5C:
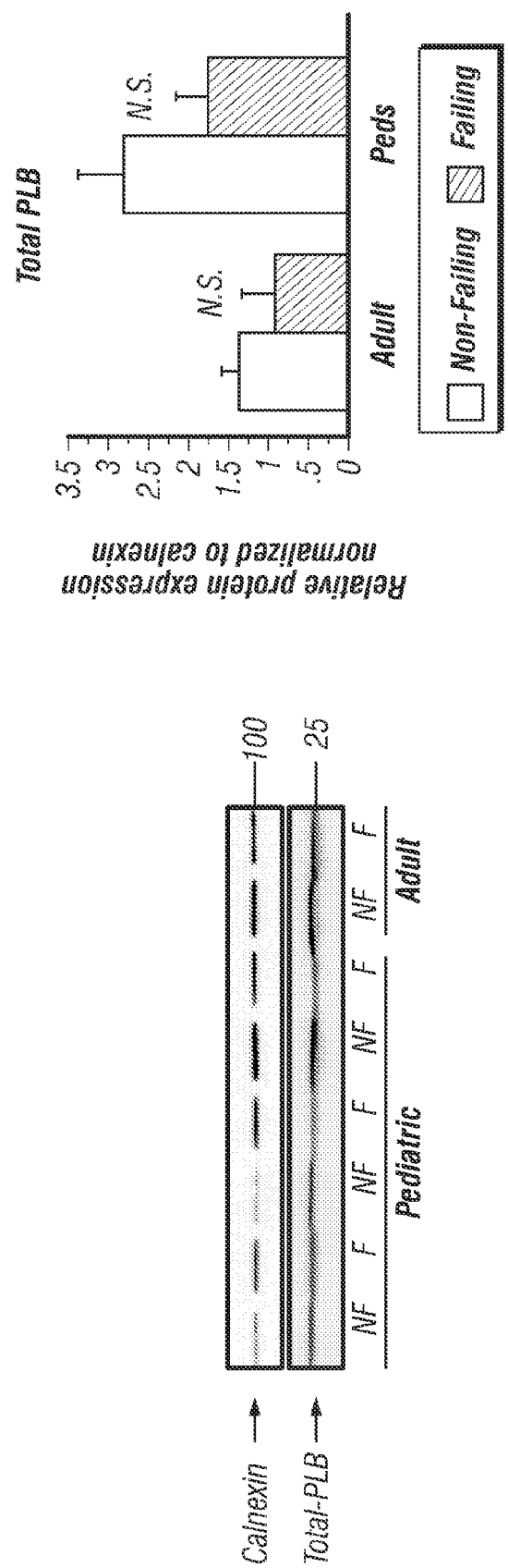

To further support that these differences affect disease mechanisms, the inventors evaluated phosphorylation of phospholamban (FIGS. 5A-C) at 2 sites. Phosphorylation of phospholamban (PLB) removes its inhibitory influence on sarcoplasmic reticulum ATPase (SERCA) and increases sarcoplasmic reticulum $Ca_{2+}$ (SR $Ca_{2+}$) reuptake as well as subsequent $Ca_{2+}$ release. The Serine 16 site is phosphorylated by PKA, while the Threonine 17 site is phosphorylated by CaMK. Both sites are known to become dephosphorylated with heart failure in human adults (FIGS. 5A-C and others (Whaley-connell et al., 2009; Bristow and Feldman, 1992)) and in animal models of heart failure (FIGS. 9A-B and others (Boknik et al., 2000)). The dephosphorylation is believed to be due increased phosphatase activity to compensate for increased kinase activity (i.e., CaMK) (Boknik et al., 2000). In contrast, there is no change in phosphorylation of either site in the pediatric heart in response to heart failure, demonstrating that the balance of kinases and phosphatases that act on phospholamban are different between adults and children.

Figure 6:
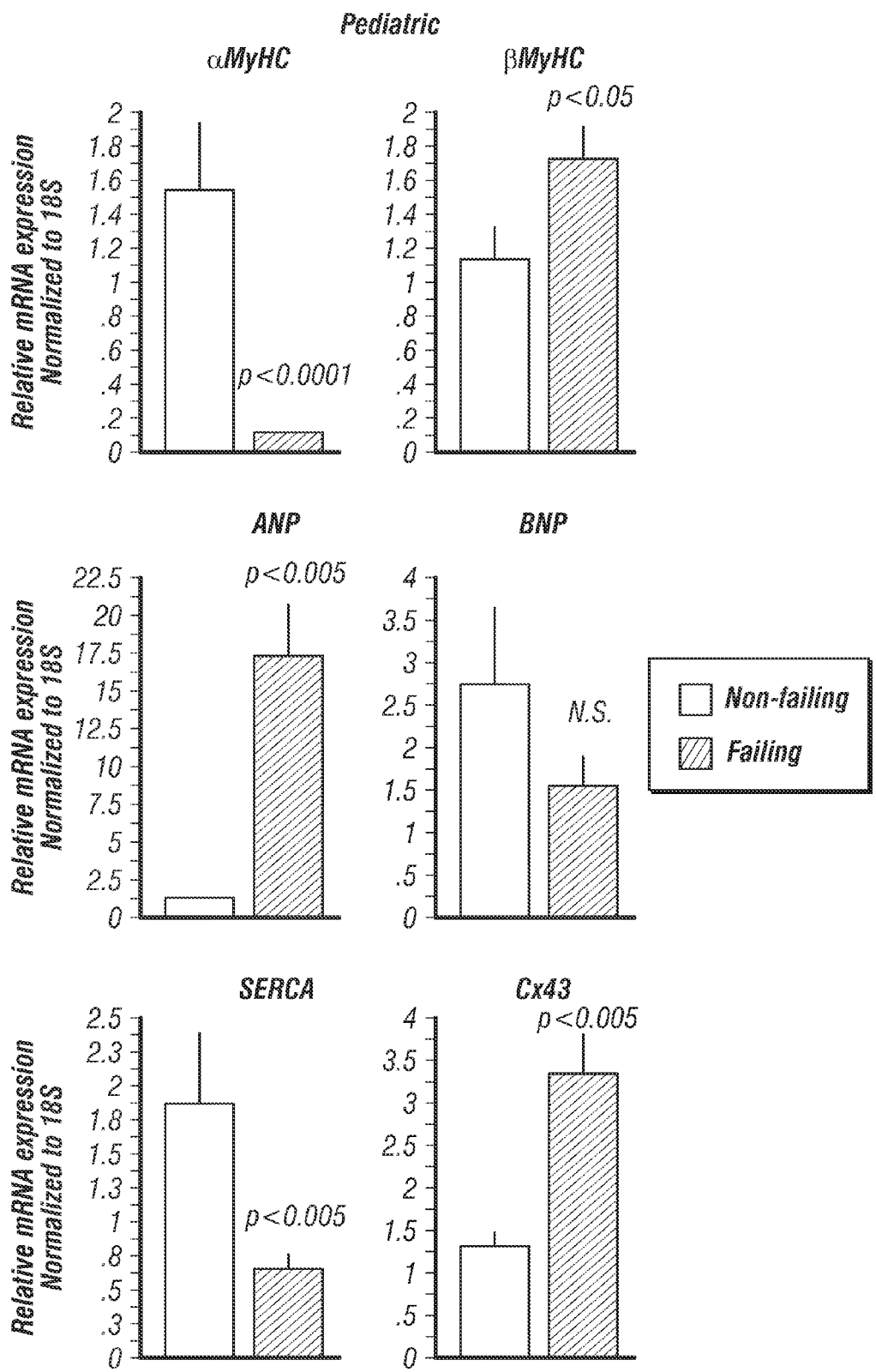
FIG. 6—Pathologic gene expression analysis. Although there are several components of the pathologic gene program that change in accordance with the adult literature (and to the adult profile demonstrated by the current experiments) BNP is unchanged in pediatric HF and connexin 43 (cx43, gap junction protein) is antithetically regulated when compared to adult HF patients. p values correspond to F to NF comparisons. (N=37 NF pediatric, 52 F pediatric, 26 NF adults, 22 F adults).
Figure 6:
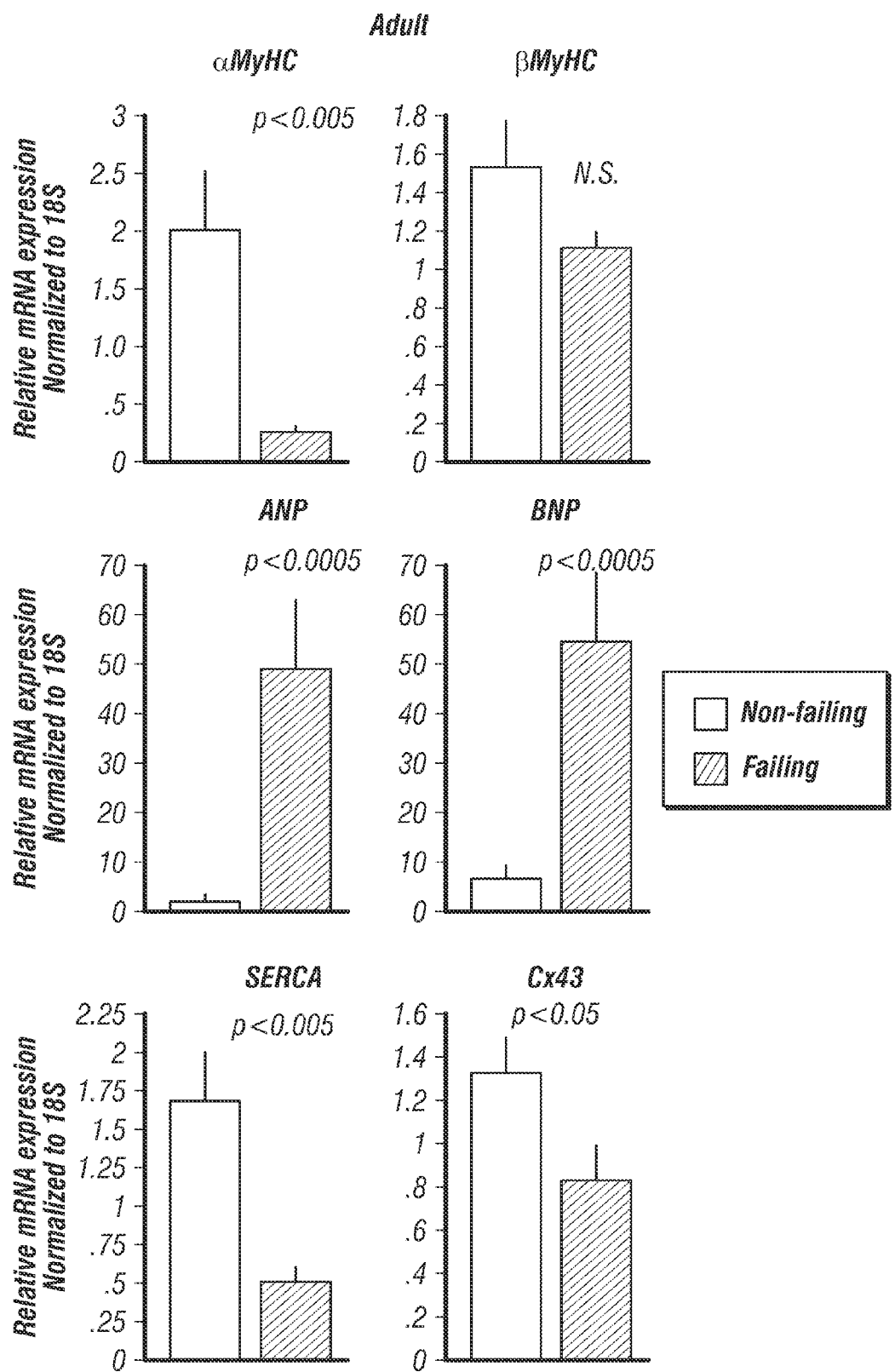
Figure 7:
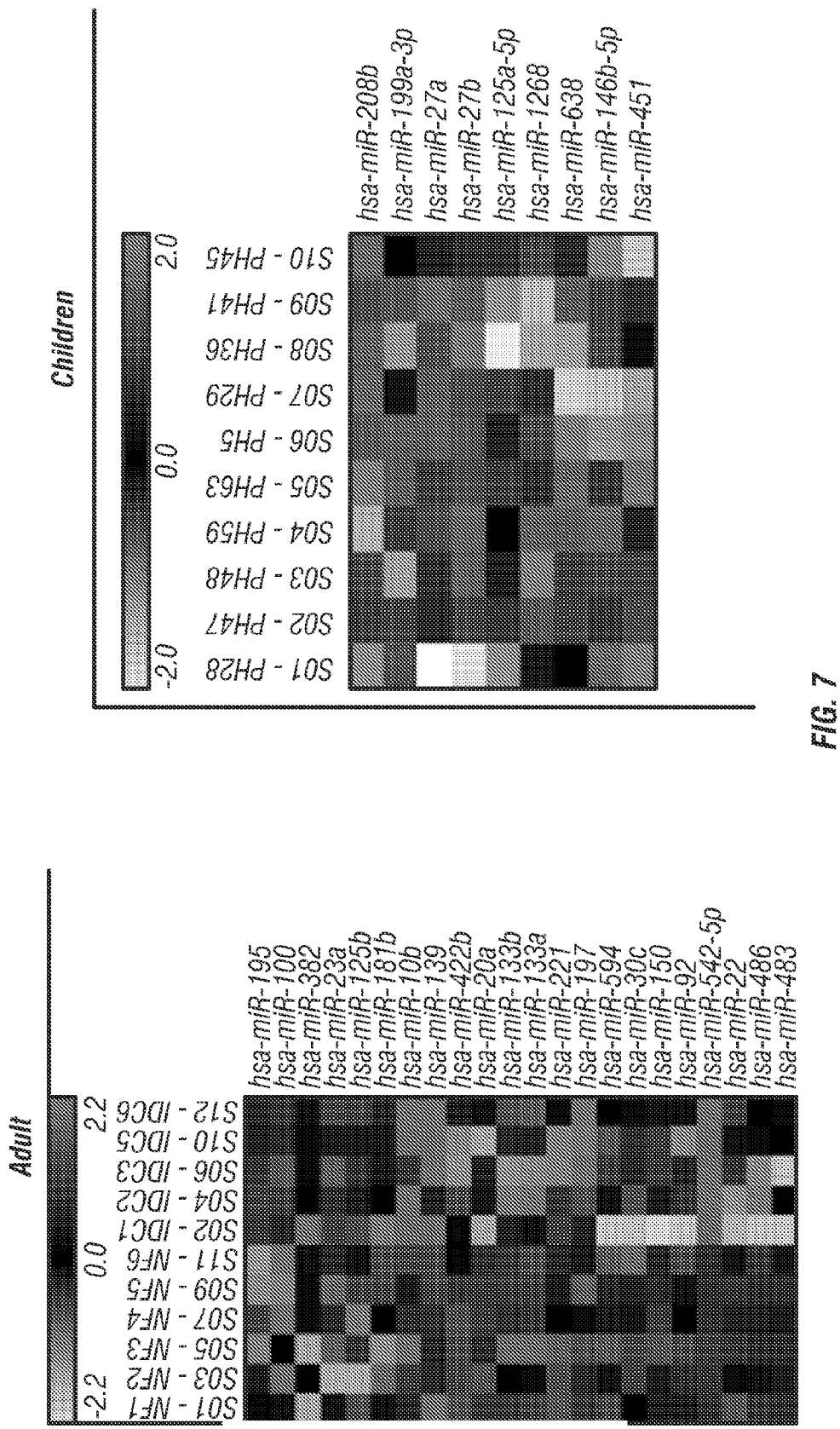
FIG. 7—miRNA expression profiles in samples obtained from non-failing (Adults-NF1-6, Children-S01-S05) and idiopathic cardiomyopathy (Adults-IDC1-6, Children-S06-S10) patients. Down-regulated miRNAs (green) and up-regulated miRNAs (red) are presented. Only miRNAs with a p-value<0.10 as determined by t-Test are shown. There is no overlap in the miRNAs that change in response to HF between adults (from our array study) and children and little overlap with what has been published by other groups (Sucharov et al., 2008; Small et al., 2010). The only miRNA that is found in both analyses is miR125 which has opposite expression profiles (up-regulated in adults and down-regulated in children) in response to heart failure.

CaMK activation is also responsible for the expression of a pathologic gene program in adults that consists of down-regulation of adult genes such as alpha-MyHC and the Sarcoplasmic reticulum ATPase (SERCA) and an upregulation of genes expressed during the fetal stage such as beta MyHC and natriuretic peptides (ANP and BNP). The pattern demonstrated in the adults in FIG. 6 recapitulates this expression pattern. Although the down-regulation of the adult genes is similar in children to the adults, the up-regulation of the natriuretic peptides is either significantly blunted (ANP) or absent (BNP). Connexin43 (Cx43) the main ventricular gap junction protein responsible for inter-cellular communication and small molecule trafficking is known to be decreased in the failing adult heart (FIG. 6 and others (Lowes et al., 2002)). This decreased plays a mechanistic role in the increased risk of ventricular arrhythmias in adults with heart failure. In contrast, Cx43 expression increases with heart failure in children (FIG. 6). It is possible that this plays a role in the lower risk of ventricular arrhythmias in children than adults with heart failure.

microRNAs (miRNA) are small non-coding RNAs that bind to the 3'UTR of targets and either repress protein expression through translational repression or transcript degradation. A broad assessment of changes in miRNA expression can be performed using a chip based approach. A number of miRNA on the chip have been shown to be regulated by heart failure in adults (FIG. 7, (Sucharov et al., 2008)). In children with heart failure miRNA regulation is unique when compared to adults. Indeed, the only miRNA that was regulated by heart failure in both groups (miR125) was up-regulated in the adults and down-regulated in the children in response to heart failure. A summary of the human age-related differences in response to heart failure first demonstrated by the inventors can be found in Table 3.

To support the claims of the beneficial effects of β1 receptor antagonists, the inventors have performed several evaluations. First, to demonstrate that the model is robust at the phenotypic level in the whole animal, pathologic cardiac growth was determined in cardiomyopathic (isoproterenol challenged) and litter-mate control young and old mice in the presence or absence of selective (β1, metoprolol) or non-selective (carvedilol) β-adrenergic receptor blockade. Isoproterenol treatment produced significant pathologic cardiac growth in both young and old mice (P<0.05). Treatment of the control mice with each β-blocker demonstrated no effect regardless of age. As demonstrated in the provisional application and FIG. 10, cardiac pathology is suppressed by both treatment paradigms in the adult mice (similar to the adult human literature (US Coreg, CAPRICORN, COPERNICUS, MERIT HF)) but non-selective β-adrenergic receptor blockade with carvedilol in the young mice showed no benefit (similar to the human Pediatric Carvedilol Trial).

Figure 10:
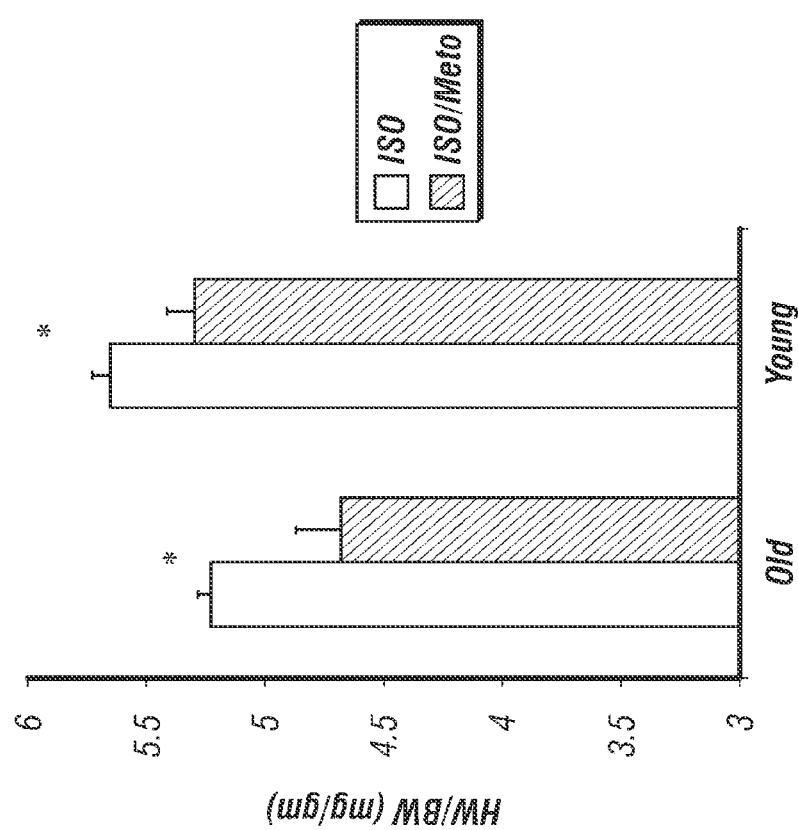
FIGS. 10—β-adrenergic blockers treatment of young and older mice under pathologic conditions recapitulates the human heart failure data. The heart weight to body weight ratio (HW/BW) is lower with both Carvedilol (Coreg) and Metoprolol (Meto) treatment in the older animals indicating a blunting of the response to ISO consistent with the evidence of benefit in human clinical trials (US Coreg Trial, COPERNICUS, CAPRICORN and MERIT HF). There was no influence of Coreg treatment on the cardiac growth response to ISO in the young animals consistent with the Pediatric Carvedilol Trial. Importantly, the growth response was blunted with Metoprolol treatment in the younger animals supporting the inventors' claim of the beneficial effects of selective β1 adrenergic receptor antagonism in the pediatric population. *P<0.05 versus same age ISO.

Importantly, β1-selective adrenergic receptor blockade with metoprolol demonstrated benefit in the young mice. Of note, the magnitude of the benefit was similar between the young and old metoprolol treated mice (FIG. 10).

Figure 9A:
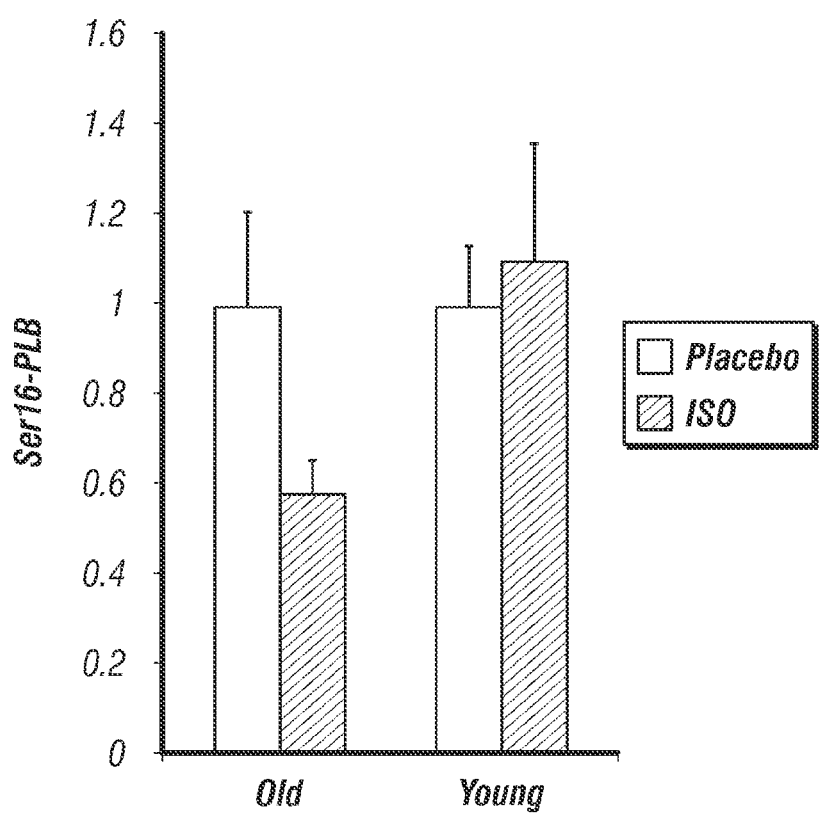

Second, to demonstrate that the model is robust at a molecular level, the inventors tested phosphorylation of phospholamban at the 2 critical sites outlined above in the cardiomyopathic (isoproterenol challenged) and control young and old mice. Similar to in humans, both serine 16 and threonine 17 were dephosphorylated in the old diseased mice but phosphorylation was unchanged at both sites in the young mice (FIGS. 9A-B). These data indicate that the signaling cascades downstream from the beta-adrenergic receptors are activated in a similar fashion in both the mouse and human supporting the validity of the model to address the therapeutic potential of the claims. There is no clinical data on the influence of β-adrenergic receptor blockade on phosphorylation of phospholamban; therefore further analysis of beta-blocker treated mice was not performed.

Figure 11:
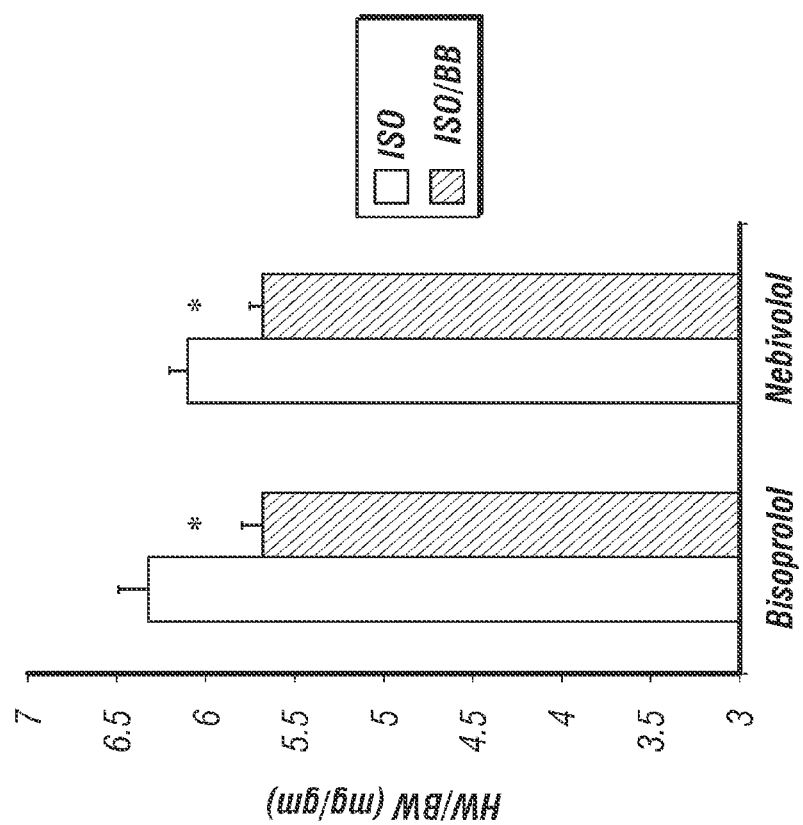
FIG. 11—β1-selective blockers suppress pathologic growth response. To demonstrate the β1 blockade class effect, young mice were treated with either Bisoprolol or Nebivolol. These compounds have higher selectivity than Metoprolol for the β1 receptor. Isoproterenol elicited a significant growth response from placebo treated animals (P<0.05 in both cohorts). Both β1-selective agents significantly suppressed the pathologic growth response to isoproterenol (*P<0.025, n=7-13 animals/group; BB=β-blocker). When combined with the data in FIG. 10, these data demonstrate the benefit of β1 selective adrenergic antagonism over nonselective adrenergic antagonism.

To demonstrate that benefits of β1-selective adrenergic receptor blockade are not limited to a single agent, the inventors treated diseased and control young mice with bisoprolol and nebivolol, two highly β1-selective antagonists. Treatment of the cardiomyopathic mice with either bisoprolol or nebivolol demonstrated significant blunting of the pathologic response with both antagonists (FIG. 11). Importantly, the magnitude of the improvement was similar to that with metoprolol.

In contrast to the β1-adrenergic receptor that is coupled only to the stimulator G-protein ($G_s$), responsible for the activation of cardiac pathology, the β2-receptor is also coupled to an inhibitory G-protein ($G_i$) that activates an intracellular pathway that is prosurvival, though phosphorylation of Akt, and anti-apoptotic, by blocking increases in Caspase 3. It has been shown that activation of the β2-receptor preferentially activates signaling through the beneficial $G_i$ pathway (Daaka, 1997). Stimulation with full β2-receptor agonists (such as epinephrine and norepinephrine in humans with heart failure or isoproterenol in the mouse model), however, produces downregulation, internalization and desensitization of the β2-receptor (January, 1997) ultimately resulting in lower signaling through this intracellular cascade (less phosphorylation of Akt) and increases in cellular markers of apoptosis (greater Caspase 3). In contrast, exogenous selective β2-receptor agonists, such as fenoterol, stimulate the receptor but produce less receptor downregulation (January, 1997), thus preserving the beneficial signaling down this intracellular cascade. Indeed, transgenic mouse models only containing the β2-receptor (β1-receptor knock out mice) are resistant to cardiac pathology (Patterson, 2004). Importantly in adult mouse models of myocardial infarction fenoterol can adequately compete with endogenous catecholamines to prevent the detrimental changes in β2-receptor expression and signaling to produce improvements in myocardial remodeling and function (Ahmet, 2004; 2005; 2008).

Figure 12A:
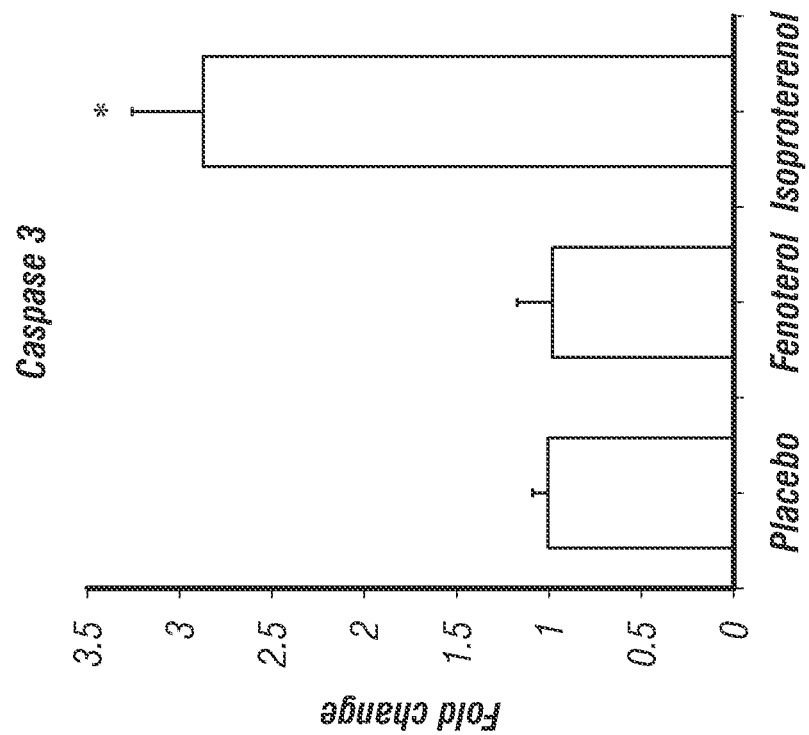
FIGS. 12A-B—β2-selective agonists activate beneficial pathways and don't stimulate apoptosis. To demonstrate the beneficial effects of β2-selective agonists, young mice were treated with fenoterol, a β2-selective agonist. To determine the influence of fenoterol on the heart, phosphorylation of Akt (a measure of activation of this beneficial pathway) and caspase 3 levels (an important initiator of apoptosis) were measured by Western blot. Fenoterol induced phosphorylation of Akt, while the pathologic stimulator isoproterenol decreased activation of this beneficial pathway. Caspase 3 levels were increased by isoproterenol treatment while fenoterol did not induce this important activator of cell death. Taken together these data demonstrate the beneficial effects of selective β2-adrenergic receptor agonism. *P<0.05 vs both other treatment groups.
Figure 12B:
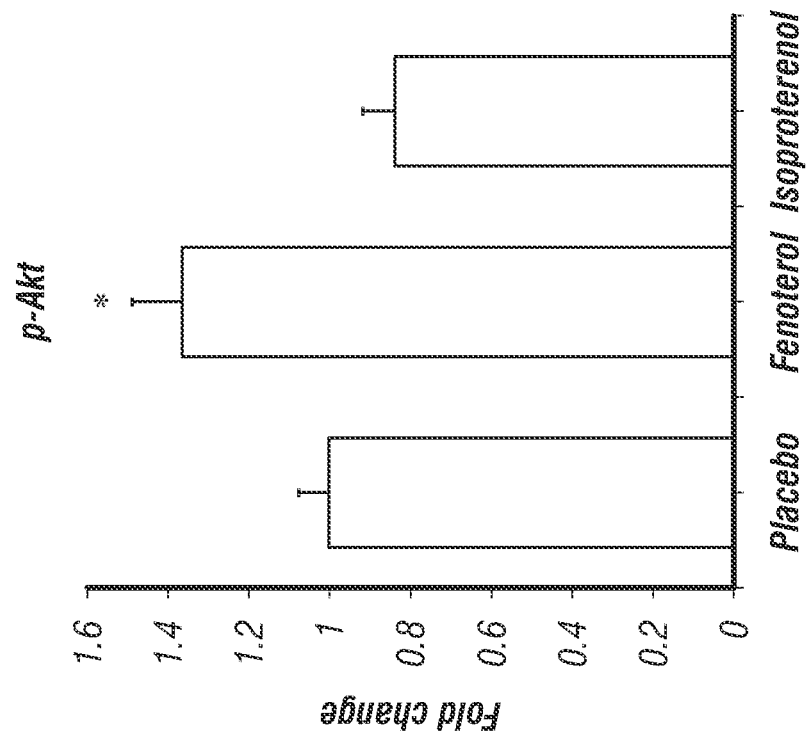

Young mice were treated with isoproterenol or fenoterol and compared to placebo treated age-matched controls. Phosphorylation of Akt and an absence of induction of Caspase 3, both beneficial outcomes, were determine in the heart follow one week of treatment (FIGS. 12A-B). The detrimental agonist isoproterenol decreased Akt phosphorylation and increased caspase 3, while in contrast, fenoterol demonstrated beneficial changes by increasing phosphorylated Akt and maintaining only basal levels of caspase 3. The combination of changes induced by isoproterenol has been demonstrated to produce cardiac pathology and cell death (Amin, 2011; Chen, 2010), while the phenotype induced by fenoterol is similar to the beneficial effects of physical activity (exercise) and the induction of beneficial cardiac adaptations (Zhang, 2007).

TABLE 3

Comparison of adult and pediatric heart failure trials and molecular changes induced by heart failure

| Clinical Trials | Adult Population | | Pediatric Population | |
|---|---|---|---|---|
| β-AR antagonist | Trial* | Outcome | Trial* | Outcome |
| Carvedilol in HF patients | US Coreg HF | Mortality Benefit 65% RR reduction | Pediatric Carvedilol Trial | No Benefit |
|  | COPERNICUS | Mortality Benefit 35% RR reduction |  |  |
|  | CAPRICORN | Mortality Benefit 23% RR reduction |  |  |
| Metoprolol in HF patients | MERIT-HF | Mortality Benefit 34% RR reduction | No Data |  |
| Bisoprolol in HF patients | CIBIS | Mortality Benefit 32% RR reduction | No Data |  |
| Nebivolol in HF patients | SENIORS | Mortality or Hospitalization Benefit 14% RR reduction | No Data |  |

| Molecular Variables | Adult Heart Failure | Pediatric Heart Failure |
|---|---|---|
| Total β-AR Protein | Decreased (Bristow et al., 1986) | Decreased |
| β1-AR Protein | Decreased (Bristow et al., 1986) | Decreased |
| β2-AR Protein | No Change (Bristow et al., 1986) | Decreased |
| β1-AR mRNA | Decreased (Lowes et al., 2002) | Increased |
| β2-AR mRNA | Decreased | No Change |

TABLE 3-continued

| | | |
|---|---|---|
| cAMP level | Decreased 60% (Bristow and Feldman, 1992) | Decreased 25% |
| CaMK Activity | Increased (Calalb et al., 2009; Hoch et al., 1999) | No Change |
| PLB-P(Serine 16) | Decreased (Chu and Kranias, 2006) | No Change |
| PLB-P(Threonine 17) | Decreased (Chu and Kranias, 2006) | No Change |
| αMyHC mRNA | Decreased (Lowes et al., 2002) | Decreased |
| βMyHC mRNA | No Change (Lowes et al., 2002) | Increased |
| ANP mRNA | Increased 50-fold (Lowes et al., 2002) | Increased 16-fold |
| BNP mRNA | Increased 50-fold (Mukoyama et al., 1991) | No Change |
| SERCA mRNA | Decreased (Lowes et al., 2002) | Decreased |
| Connexin43 mRNA | Decreased (Ai and Pogwizd, 2005) | Increased |
| microRNA: 195, 100, 382, 23a, 181b | Increased (Sucharov et al., 2008; Small et al., 2010) | No Change |
| microRNA: 125a/b | Increased (Sucharov et al., 2008; Small et al., 2010; Calalb et al., 2009) | Decreased |
| microRNA: 10b, 139, 422b, 20a, 133b, 133a, 221, 197, 594, 30c, 150 92, 542, 22, 486, 483 | Decreased (Sucharov et al., 2008; Small et al., 2010) | No Change |
| microRNA: 208b, 199a, 27a, 27b | No Change (Sucharov et al., 2008; Small et al., 2010) | Increased |
| microRNA: 1268, 638, 146b, 451 | No Change (Sucharov et al., 2008; Small et al., 2010) | Decreased |

Trial* - multicenter randomized trial data; AR—adrenergic receptor; cAMP—cyclic adenosine monophosphate; CaMK—calcium-calmodulin kinase; PLB-P—phosphorylation of phospholamban (Site); MyHC—myosin heavy chain; ANP—atrial natriuretic peptide; BNP—brain natriuretic peptide; SERCA—sarcoplasmic reticulum ATPase; Decreased-lower expression/activity in samples from patients with
heart failure than nonfailing samp; Increased-higher expression/activity in samples from patients with heart failure than nonfailing samples.
All changes (increased/decreased/no change) listed in the "Molecular Variables" section are those demonstrated by the inventors. Citations of literature demonstrating similar findings in the adult population are also listed.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference.

U.S. Pat. No. 5,604,251
U.S. Ser. 61/377,277
Ai and Pogwizd, *Circ. Res.*, 96:54-63, 2005.
Ahmet et al., *Heart Failure Rev.*, 10:289-296, 2005.
Ahmet et al. *Circulation*, 110:1083-1090, 2004.
Ahmet et al., *JPET* 325:491-499, 2008.
Amin, J. *Signal Transd.*, doi. 10.1155/2011/179057, 2011.
Bartholomeu et al., *J. Mol. Cell. Cardiol.*, 45:240-249, 2008.
Boknik et al., *Naunyn. Schmiedebergs Arch. Pharmacol.*, 362:222-231, 2000.
Bristow and Feldman, *Basic Res. Cardiol.*, 87(Suppl 1):15-35, 1992.
Bristow et al., *Circ. Res.*, 59:297-309, 1986.
Bristow et al., *J. Clin. Invest.*, 74:212-223, 1984.
Bristow, *Cardiology*, 92:3-6, 1999.
Brodde et al., *Naunyn Schmiedebergs Arch. Pharmacol.*, 344:430-436, 1991.
Calalb et al., *Clin. Transl. Sci.*, 2:325-332, 2009.
CAPRICORN: *Lancet.*, 357:1385-1390, 2001.
Chen, *Basic Res. Cardiol.*, 105:573-81, 2010.
Chu and Kranias, *Novartis Found Symp.*, 274:156-171, 2006.
CIBIS: *Lancet.*, 353(9146):9-13, 1999.
COPERNICUS: *New England J. Med.*, 344:1651-1658, 2001.
Daaka, *Nature* 390:88-91, 1997.
Dalla Libera et al., *Int. J. Cardiol.*, 143:192-199, 2010.
Durand et al., *Ann. Med.*, 27:311-317, 1995.
Eichhorn and Bristow, *Circulation*, 94:2285-2296, 1996.
Harding et al., *Proc. Natl. Acad. Sci. USA*, 98:5809-5814, 2001.
Hoch et al., *Circ. Res.*, 84:713-721, 1999.
January, *J. Biol. Chem.*, 272:23871-79, 1997.
Kirchhefer et al., *Cardiovasc. Res.*, 42:254-261, 1999.
Lowes et al., *J. Clin. Invest.*, 100:2315-2324, 1997.
Lowes et al., *N. Engl. J. Med.*, 346:1357-1365, 2002.
MERIT-HF: *Lancet.*, 353(9169):2001-2007, 1999.
Milting et al., *J. Mol. Cell. Cardiol.*, 41:441-450, 2006.
Mukoyama et al., *J. Clin. Invest.*, 87:1402-1412, 1991.
Patterson, *Crit. Care Med.*, 32:1041-8, 2004.
PCT Appln. WO 98/33791
Pediatric Carvedilol Trial: *J. Amer. Med. Assoc.*, 298:1171-1179, 2007.
Remington's Pharmaceutical Sciences, 15th Ed., 1035-1038 and 1570-1580, 1990.
SENIORS: *Eur. Heart J.*, 26(3):215-225, 2005.

Small et al., *Circulation*, 121:1022-1032, 2010.
Sucharov et al., *J. Biol. Chem.*, 278:31233-31239, 2003.
Sucharov et al., *J. Mol. Cell. Cardiol.*, 45:185-192, 2008.
US Coreg HF: *New England J. Med.*, 334:1349-1355, 1996.
Whaley-Connell et al., *Am. J. Nephrol.*, 30:354-360, 2009.
Zhang, *Apoptosis*, 12:1579-88, 2007.

What is claimed is:

1. A method of treating dilated cardiomyopathy in a pediatric subject comprising administering to said subject an effective amount of a β1-adrenergic receptor-selective antagonist, wherein said β1-adrenergic receptor-selective antagonist is at least twice as β1-selective as Metoprolol.

2. The method of claim 1, wherein said pediatric subject is less than 15 years of age.

3. The method of claim 1, wherein said β1-selective adrenergic receptor antagonist is selected from Nebivolol, CPG 20712A, ICI 89406, Practolol, Xamoterol, Bisoprolol, Betaxolol or Atenolol.

4. The method of claim 1, wherein said β1-adrenergic receptor-selective antagonist is administered orally, transdermally, in sustained release, in controlled release, in delayed release, as a suppository, or sublingually.

5. The method of claim 1, wherein said β1-adrenergic receptor-selective antagonist is administered intravenously, subcutaneously, or intraosseously.

6. The method of claim 1, wherein said subject is administered a second therapy for dilated cardiomyopathy.

7. The method of claim 6, wherein said second therapy is selected from the group consisting of an inotrope, a diuretic, ACE-I, AII antagonist, BNP, a $Ca^{++}$-blocker, or an HDAC inhibitor.

8. The method of claim 6, wherein said second therapy is a β2-adrenergic receptor-selective agonist.

9. The method of claim 1, wherein said β2-adrenergic receptor-selective agonist is albuterol, levoalbuterol, terbutaline, pirbuterol, procaterol, metaproterenol, fenoterol, bitolterol mesylate, ritodrine, salmeterol, formoterol, bambuterol, clenbuterol or indacaterol.

10. The method of claim 6, wherein said second therapy is administered at the same time as said β1-adrenergic receptor-selective antagonist.

11. The method of claim 6, wherein said second therapy is administered either before or after said β1-adrenergic receptor-selective antagonist.

12. The method of claim 1, wherein said one or more improved symptoms comprises increased exercise capacity, increased cardiac ejection volume, decreased left ventricular end diastolic pressure, decreased pulmonary capillary wedge pressure, increased cardiac output, or cardiac index, lowered pulmonary artery pressures, decreased left ventricular end systolic and diastolic dimensions, decreased left and right ventricular wall stress, decreased wall tension, increased quality of life, and decreased disease-related morbidity or mortality.

* * * * *